United States Patent
Yokoyama et al.

(10) Patent No.: US 9,905,770 B2
(45) Date of Patent: Feb. 27, 2018

(54) COMPOUND HAVING ACRIDAN RING STRUCTURE, AND ORGANIC ELECTROLUMINESCENT DEVICE

(75) Inventors: Norimasa Yokoyama, Tokyo (JP); Makoto Nagaoka, Tsukuba (JP); Naoaki Kabasawa, Tokyo (JP); Eiji Takahashi, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 794 days.

(21) Appl. No.: 14/113,280

(22) PCT Filed: Apr. 24, 2012

(86) PCT No.: PCT/JP2012/002789
§ 371 (c)(1),
(2), (4) Date: Oct. 22, 2013

(87) PCT Pub. No.: WO2012/147330
PCT Pub. Date: Nov. 1, 2012

(65) Prior Publication Data
US 2014/0042425 A1    Feb. 13, 2014

(30) Foreign Application Priority Data
Apr. 27, 2011 (JP) .................. 2011-099064

(51) Int. Cl.
| | | |
|---|---|---|
| H01L 51/00 | (2006.01) | |
| C07D 219/02 | (2006.01) | |
| C07D 221/20 | (2006.01) | |
| C07D 401/04 | (2006.01) | |
| C07D 409/04 | (2006.01) | |
| C07D 409/10 | (2006.01) | |
| C07D 409/14 | (2006.01) | |
| C09K 11/06 | (2006.01) | |
| H05B 33/14 | (2006.01) | |
| H01L 51/50 | (2006.01) | |

(52) U.S. Cl.
CPC ........ *H01L 51/0052* (2013.01); *C07D 219/02* (2013.01); *C07D 221/20* (2013.01); *C07D 401/04* (2013.01); *C07D 409/04* (2013.01); *C07D 409/10* (2013.01); *C07D 409/14* (2013.01); *C09K 11/06* (2013.01); *H01L 51/006* (2013.01); *H01L 51/0058* (2013.01); *H01L 51/0059* (2013.01); *H01L 51/0061* (2013.01); *H01L 51/0068* (2013.01); *H01L 51/0072* (2013.01); *H01L 51/0074* (2013.01); *H05B 33/14* (2013.01); *C09K 2211/1007* (2013.01); *C09K 2211/1011* (2013.01); *C09K 2211/1029* (2013.01); *C09K 2211/1088* (2013.01); *H01L 51/5056* (2013.01); *H01L 51/5088* (2013.01)

(58) Field of Classification Search
CPC .................. H01L 51/0072; H01L 51/0058
See application file for complete search history.

(56) References Cited

U.S. PATENT DOCUMENTS

| | | | |
|---|---|---|---|
| 2004/0219386 A1* | 11/2004 | Thoms ................. | C07D 221/20 428/690 |
| 2012/0168730 A1 | 7/2012 | Kim et al. | |
| 2012/0181524 A1 | 7/2012 | Kato et al. | |
| 2012/0273766 A1 | 11/2012 | Kato et al. | |
| 2012/0319052 A1* | 12/2012 | Brocke ................ | C07D 401/04 252/500 |
| 2013/0075715 A1 | 3/2013 | Yokoyama et al. | |
| 2014/0061548 A1 | 3/2014 | Montenegro et al. | |

FOREIGN PATENT DOCUMENTS

| | | |
|---|---|---|
| JP | 2011-210749 A | 10/2011 |
| JP | 2012 530796 * | 12/2012 |
| JP | 5850835 B2 | 2/2016 |

(Continued)

OTHER PUBLICATIONS

JP 2012 530796 machine translation (2012).*
Office Action dated May 24, 2016, issued for the corresponding Japanese patent application No. 2013-511923.
Supplementary European Search Report dated Sep. 25, 2014, issued for the corresponding European patent application No. 12 77 6870.3.

(Continued)

*Primary Examiner* — Kuo-Liang Peng
(74) *Attorney, Agent, or Firm* — Locke Lord LLP; James E. Armstrong, IV; Nicholas J. DiCeglie, Jr.

(57) ABSTRACT

An organic compound having a substituted acridan ring structure with characteristics excelling in hole-injecting/transporting performance and having an electron blocking ability, a highly stable thin-film state, and excellent heat resistance is provided as a material for an organic electroluminescent device of high efficiency and high durability, and the organic electroluminescent device of high efficiency and high durability is provided using this compound. The compound is used as a constituent material of at least one organic layer in the organic electroluminescent device that includes a pair of electrodes and one or more organic layers sandwiched between the pair of electrodes.

[Chemical Formula 1]

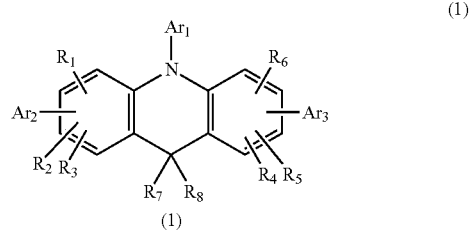

(1)

16 Claims, 4 Drawing Sheets

(56) References Cited

FOREIGN PATENT DOCUMENTS

| TW | 201112469 A | | 4/2011 |
|---|---|---|---|
| WO | WO-2006/033563 A1 | | 3/2006 |
| WO | 2010 147425 | * | 12/2010 |
| WO | WO-2010/147319 A2 | | 12/2010 |
| WO | WO-2010/147425 A2 | | 12/2010 |
| WO | 2011 107186 | * | 9/2011 |
| WO | WO-2011/107186 A2 | | 9/2011 |
| WO | WO-2011/155169 A1 | | 12/2011 |
| WO | WO-2012/029253 A1 | | 3/2012 |
| WO | WO-2012/049828 A1 | | 4/2012 |
| WO | WO-2012/150001 A1 | | 11/2012 |

OTHER PUBLICATIONS

Office Action dated Nov. 5, 2015, issued for the Taiwanese patent application No. 101114961 and Japanese translation thereof.
International Search Report dated May 22, 2012, issued for PCT/JP2012/002789.

\* cited by examiner

COMPOUND HAVING ACRIDAN RING STRUCTURE, AND ORGANIC ELECTROLUMINESCENT DEVICE

TECHNICAL FIELD

The present invention relates to compounds suited for an organic electroluminescent device, a preferred self light-emitting device for various display devices, and to the device. Specifically, the invention relates to compounds having an acridan ring structure, and to organic electroluminescent devices that use the compounds.

BACKGROUND ART

The organic electroluminescent device is a self-emitting device, and has been actively studied for their brighter, superior viewability and ability to display clearer images compared with the liquid crystal device.

In 1987, C. W. Tang et al. at Eastman Kodak developed a laminated structure device using materials assigned with different roles, realizing practical applications of an organic electroluminescent device with organic materials. These researchers laminated an electron-transporting phosphor which is tris(8-hydroxyquinoline)aluminum (hereinafter referred to as $Alq_3$) and a hole-transporting aromatic amine compound, and injected the both charges into the phosphor layer to cause emission in order to obtain a high luminance of 1,000 $cd/m^2$ or more at a voltage of 10 V or less (refer to Patent Documents 1 and 2, for example).

To date, various improvements have been made for practical applications of the organic electroluminescent device. In order to realize high efficiency and durability, various roles are further subdivided to provide an electroluminescence device that includes an anode, a hole injection layer, a hole transport layer, a light emitting layer, an electron transport layer, an electron injection layer, and a cathode successively formed on a substrate (refer to Non-Patent Document 1, for example).

Further, there have been attempts to use triplet excitons for further improvements of luminous efficiency, and use of phosphorescent materials has been investigated (refer to Non-Patent Document 2, for example).

The light emitting layer can be also fabricated by doping a charge-transporting compound, generally called a host material, with a phosphor or a phosphorescent material. As described in the foregoing Lecture Preprints, selection of organic materials in an organic electroluminescent device greatly influences various device characteristics, including efficiency and durability.

In an organic electroluminescent device, the charges injected from the both electrodes recombine at the light emitting layer to cause emission. What is important here is how efficiently the hole and electron charges are transferred to the light emitting layer. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and the amorphousness of the materials are also important with respect to a lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (hereinafter referred to as NPD) and various aromatic amine derivatives are known as the hole transport materials used for the organic electroluminescent device (refer to Patent Documents 1 and 2, for example). Although NPD has desirable hole transportability, it has a low glass transition point (Tg) of 96° C. which is an index of heat resistance and therefore causes the degradation of device characteristics by crystallization under a high-temperature condition (refer to Non-Patent Document 3, for example). The aromatic amine derivatives described in the Patent Documents 1 and 2 include a compound known to have an excellent hole mobility of $10^{-3}$ $cm^2/Vs$ or higher. However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency.

Arylamine compounds of the following formulae having a substituted acridan structure (for example, Compounds A and B) are proposed as compounds improved in the characteristics such as heat resistance, hole injectability and electron blocking performance (refer to Patent Documents 3 and 4, for example).

[Chemical Formula 1]

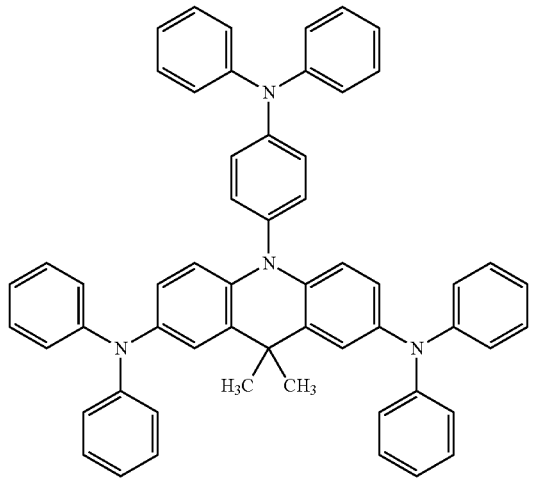

(Compound A)

[Chemical Formula 2]

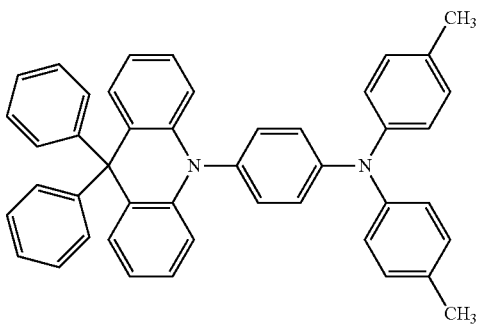

(Compound B)

However, while the devices using these compounds for the hole injection layer or the hole transport layer have been improved in heat resistance, luminous efficiency and the like, the improvements are still insufficient. Further, it cannot be said to have a sufficiently low driving voltage and sufficient current efficiency, and there is a problem also in amorphousness. Further improvements of a low driving voltage and luminous efficiency while increasing amorphousness are therefore needed.

CITATION LIST

Patent Documents

Patent Document 1: JP-A-8-48656
Patent Document 2: Japanese Patent No. 3194657
Patent Document 3: WO2006/033563
Patent Document 4: WO2007/110228

Non Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Organic EL Symposium, the 3rd Regular presentation Preprints, pp. 13 to 14 (2006)
Non-Patent Document 4: J. Org. Chem., 60, 7508 (1995)
Non-Patent Document 5: Chem. Rev., 95, 2457 (1995)

SUMMARY OF THE INVENTION

Problems that the Invention is to Solve

An object of the present invention is to provide an organic compound with characteristics excelling in hole-injecting/transporting performance and having electron blocking ability, high stability in a thin-film state and excellent heat resistance, the organic compound being provided as material for an organic electroluminescent device having high efficiency add high durability. This invention also provides the organic electroluminescent device of high efficiency and high durability using this compound.

Physical properties of the organic compound to be provided by the present invention include (1) good hole injection characteristics, (2) large hole mobility, (3) excellent electron blocking ability, (4) stability in the thin-film state, and (5) excellent heat resistance. Physical properties of the organic electroluminescent device to be provided by the present invention include (1) high luminous efficiency and high power efficiency, (2) low turn on voltage, and (3) low actual driving voltage.

In order to achieve the above objects, the present inventors designed compounds having an acridan ring structure in anticipation of the high hole-injecting/transporting ability of an aromatic tertiary amine structure, the electron blocking performance of the acridan ring structure, and the effect of heat resistance and thin-film stability of these partial structures. The present inventors produced various test organic electroluminescent devices using the compounds chemically synthesized to have the acridan ring structure, and the present invention was completed after thorough evaluations of the device characteristics.

Specifically, the present invention is a compound of the following general formula (1) having an acridan ring structure.

[Chemical Formula 3]

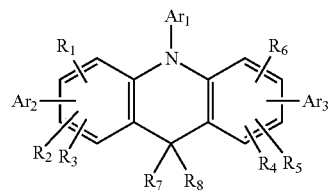

(1)

In the formula, $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_6$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and may bind to each other via a single bond, substituted or unsubstituted methylene, an oxygen atom, or a sulfur atom to form a ring. $R_7$ and $R_8$ may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, or cycloalkyloxy of 5 to 10 carbon atoms that may have a substituent, and may bind to each other via a single bond, substituted or unsubstituted methylene, an oxygen atom, or a sulfur atom to form a ring.

The present invention is a compound of the following general formula (2) having an acridan ring structure.

[Chemical Formula 4]

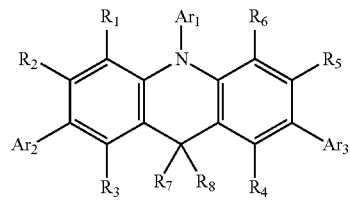

(2)

In the formula, $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, $R_1$ to $R_6$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and may bind to each other via a single bond, substituted or unsubstituted methylene, an oxygen atom, or a sulfur atom to form a ring. $R_7$ and $R_8$ may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, or cycloalkyloxy of 5 to 10 carbon atoms that may have a substituent, and may bind to each other via a single bond, substituted or unsubstituted methylene, an oxygen atom, or a sulfur atom to form a ring.

The present invention is a compound of the general formula (1) having an acridan ring structure in which $R_7$ and $R_8$ are methyl.

The present invention is a compound of the general formula (1) having an acridan ring structure in which $Ar_1$ is substituted or unsubstituted biphenylyl.

The present invention is a compound of the general formula (1) having an acridan ring structure in which $Ar_1$ is substituted or unsubstituted 9,9'-dimethylfluorenyl.

The present invention is a compound of the general formula (1) having an acridan ring structure in which $Ar_1$ is 9-phenyl-9H-carbazolyl.

The present invention is an organic electroluminescent device that includes a pair of electrodes, and one or more organic layers sandwiched between the pair of electrodes, wherein the compound of the general formula (1) or (2) having an acridan ring structure is used as a constituent material of at least one of the organic layers.

Specific examples of the "linear or branched alkyl of 1 to 6 carbon atoms", "cycloalkyl of 5 to 10 carbon atoms", or "linear or branched alkenyl of 2 to 6 carbon atoms" in the "linear or branched alkyl of 1 to 6 carbon atoms that may have a substituent", "cycloalkyl of 5 to 10 carbon atoms that may have a substituent", or "linear or branched alkenyl of 2 to 6 carbon atoms that may have a substituent" represented by $R_1$ to $R_8$ in general formulae (1) and (2) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "substituted linear or branched alkyl of 1 to 6 carbon atoms", "substituted cycloalkyl of 5 to 10 carbon atoms", or "substituted linear or branched alkenyl of 2 to 6 carbon atoms" represented by $R_1$ to $R_8$ in general formulae (1) and (2) include a deuterium atom, trifluoromethyl, cyano, nitro; halogen atoms such as a fluorine atom, a chlorine atom, a bromine atom, and an iodine atom; linear or branched alkoxy of 1 to 6 carbon atoms such as methoxy, ethoxy, and propyloxy; alkenyl such as allyl; aryloxy such as phenoxy and tolyloxy; arylalkoxy such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, pyranyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These substituents may be further substituted with other substituents. Further, these substituents may bind to each other via a single bond, substituted or unsubstituted methylene, an oxygen atom, or a sulfur atom to form a ring.

Specific examples of the "linear or branched alkyloxy of 1 to 6 carbon atoms" or "cycloalkyloxy of 5 to 10 carbon atoms" in the "linear or branched alkyloxy of 1 to 6 carbon atoms that may have a substituent" or "cycloalkyloxy of 5 to 10 carbon atoms that may have a substituent" represented by $R_1$ to $R_8$ in general formulae (1) and (2) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "substituted linear or branched alkyloxy of 1 to 6 carbon atoms" or "substituted cycloalkyloxy of 5 to 10 carbon atoms" represented by $R_1$ to $R_8$ in general formulae (1) and (2) include a deuterium atom, trifluoromethyl, cyano, nitro; halogen atoms such as a fluorine atom, a chlorine atom, a bromine atom, and an iodine atom; linear or branched alkoxy of 1 to 6 carbon atoms such as methoxy, ethoxy, and propyloxy; alkenyl such as allyl; aryloxy such as phenoxy and tolyloxy; arylalkoxy such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, pyranyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These substituents may be further substituted with other substituents. Further, these substituents may bind to each other via a single bond, substituted or unsubstituted methylene, an oxygen atom, or a sulfur atom to form a ring.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $R_1$ to $R_6$ in general formula (1) and (2) include phenyl, biphenylyl, terphenylyl, naphthyl, anthryl, phenanthryl, fluorenyl, indenyl, pyrenyl, perylenyl, fluoranthenyl, triphenylenyl, pyridyl, furyl, pyranyl, thienyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These groups may bind to each other via a single bond, substituted or unsubstituted methylene, an oxygen atom, or a sulfur atom to form a ring.

It is preferable that the "aromatic heterocyclic group" in the "substituted or unsubstituted aromatic heterocyclic group" represented by $R_1$ to $R_6$ in general formulae (1) and (2) is a sulfur-containing aromatic heterocyclic group such as thienyl, benzothienyl, benzothiazolyl, and dibenzothienyl.

Specific examples of the "substituent" in the "substituted aromatic hydrocarbon group", "substituted aromatic heterocyclic group", or "substituted condensed polycyclic aromatic group" represented by $R_1$ to $R_6$ in general formulae (1) and (2) include a deuterium atom, trifluoromethyl, cyano, nitro; halogen atoms such as a fluorine atom, a chlorine atom, a bromine atom, and an iodine atom; linear or branched alkyl of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxy of 1 to 6 carbon atoms such as methoxy, ethoxy, and propyloxy; alkenyl such as allyl; aralkyl such as benzyl, naphthylmethyl, and phenethyl; aryloxy such as phenoxy and tolyloxy; arylalkoxy such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, pyranyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl; arylvinyl such as styryl and naphthylvinyl; and acyl such as acetyl and benzoyl. These substituents may be further substituted. Further, these substituents may bind to each other via a single bond, substituted or unsubstituted methylene, an oxygen atom, or a sulfur atom to form a ring.

Specific examples of the "aryloxy" in the "substituted or unsubstituted aryloxy" represented by $R_1$ to $R_6$ in general formulae (1) and (2) include phenoxy, tolyloxy, biphenylyloxy, terphenylyloxy, naphthyloxy, anthryloxy, phenanthryloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

Specific examples of the "substituent" in the "substituted aryloxy" represented by $R_1$ to $R_6$ in general formulae (1) and (2) include a deuterium atom, trifluoromethyl, cyano, nitro; halogen atoms such as a fluorine atom, a chlorine atom, a bromine atom, and an iodine atom; linear or branched alkyl of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxy of 1 to 6 carbon atoms such as methoxy, ethoxy, and propyloxy; alkenyl such as allyl; aralkyl such as benzyl, naphthylmethyl, and phenethyl; aryloxy such as phenoxy and tolyloxy; arylalkoxy such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, pyranyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl; arylvinyl such as styryl and naphthylvinyl; and acyl such as acetyl and benzoyl. These substituents may be further substituted. Further, these substituents may bind to each other via a single bond, substituted or unsubstituted methylene, an oxygen atom, or a sulfur atom to form a ring.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_3$ in general formulae (1) and (2) include phenyl, biphenylyl, terphenylyl, naphthyl, anthryl, phenanthryl, fluorenyl, indenyl, pyrenyl, perylenyl, fluoranthenyl, triphenylenyl, pyridyl, furyl, pyranyl, thienyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl.

It is preferable that the "aromatic heterocyclic group" in the "substituted or unsubstituted aromatic heterocyclic group" represented by $Ar_1$ to $Ar_3$ in general formulae (1) and (2) is a sulfur-containing aromatic heterocyclic group such as thienyl, benzothienyl, benzothiazolyl, and dibenzothienyl, and carbazolyl having a substituent at the ninth position.

Specific examples of the "substituent" in the "substituted aromatic hydrocarbon group", "substituted aromatic heterocyclic group", or "substituted condensed polycyclic aromatic group" represented by $Ar_1$ to $Ar_3$ in general formulae (1) and (2) include a deuterium atom, trifluoromethyl, cyano, nitro; halogen atoms such as a fluorine atom, a chlorine atom, a bromine atom, and an iodine atom; linear or branched alkyl of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxy of 1 to 6 carbon atoms such as methoxy, ethoxy, and propyloxy; alkenyl such as allyl; aralkyl such as benzyl, naphthylmethyl, and phenethyl; aryloxy such as phenoxy and tolyloxy; arylalkoxy such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, pyranyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl; arylvinyl such as styryl and naphthylvinyl; and acyl such as acetyl and benzoyl. These substituents may be further substituted. Further, these substituents may bind to each other, or to the "substituted aromatic hydrocarbon group", "substituted aromatic heterocyclic group", or "substituted condensed polycyclic aromatic group" represented by $Ar_1$ to $Ar_3$ via a single bond, substituted or unsubstituted methylene, an oxygen atom, or a sulfur atom to form a ring.

It is preferable that $R_7$ and $R_8$ in general formulae (1) and (2) are "linear or branched alkyl of 1 to 6 carbon atoms that may have a substituent", particularly preferably methyl, ethyl, and propyl.

It is preferable that $Ar_1$ to $Ar_3$ in general formulae (1) and (2) are "substituted or unsubstituted aromatic hydrocarbon groups", "substituted or unsubstituted condensed polycyclic aromatic groups", or "carbazolyl groups having a substituent at the ninth position", particularly preferably substituted or unsubstituted phenyl, substituted or unsubstituted biphenylyl, substituted or unsubstituted terphenylyl, substituted or unsubstituted naphthyl, substituted or unsubstituted phenanthryl, 9,9'-dimethylfluorenyl, 9-phenyl-9H-carbazolyl, and substituted or unsubstituted triphenylenyl.

The compounds of general formulae (1) and (2) having an acridan ring structure of the present invention are novel compounds and have superior electron blocking ability, superior amorphousness and a more stable thin-film state compared to conventional hole transport materials.

The compounds of general formulae (1) and (2) having an acridan ring structure of the present invention can be used as a constituent material of the hole injection layer and/or hole transport layer of an organic electroluminescent device (hereinafter referred to as an organic EL device). With the use of material having higher hole injectability, higher mobility, higher electron blocking performance and higher stability to electrons than conventional materials, excitons generated in a light emitting layer can be confined, and the probability of hole-electron recombination can be improved. This improves luminous efficiency, lowers driving voltage and thus improves the durability of the organic EL device.

The compounds of general formulae (1) and (2) having an acridan ring structure of the present invention can also be used as a constituent material of the electron blocking layer of an organic EL device. With the use of material having an excellent electron blocking ability and having superior hole transportability and higher stability in a thin-film state than conventional materials, driving voltage is lowered and current resistance is improved while maintaining high luminous efficiency. As a result, the maximum emission luminance of the organic EL device is improved.

The compounds of general formulae (1) and (2) having an acridan ring structure of the present invention can also be used as a constituent material of the light emitting layer of the organic EL device. The material of the present invention having superior hole transportability and a wider band gap than conventional materials is used as the host material of the light emitting layer in order to form the light emitting layer by carrying a fluorescent material or phosphorescent material called a dopant. In this way, the organic EL device with a low driving voltage and improved luminous efficiency can be achieved.

The high efficiency and high durability of the organic EL device in the present invention can be achieved because of the use of the compound having an acridan ring structure, which has greater hole mobility, superior electron blocking ability and superior amorphousness than conventional hole transport materials as well as a stable thin-film state.

EFFECTS OF THE INVENTION

The compound having an acridan ring structure of the present invention is useful as the constituent material of the hole injection layer, hole transport layer, electron blocking layer, or light emitting layer of the organic EL device. The compound has an excellent electron blocking ability and satisfactory amorphousness, and excels in heat resistance as well as a stable thin-film state. The organic EL device of the present invention has high luminous efficiency and high power efficiency, and the actual driving voltage of the device can thereby be lowered.

MADE FOR CARRYING OUT THE INVENTION

Figure 1:
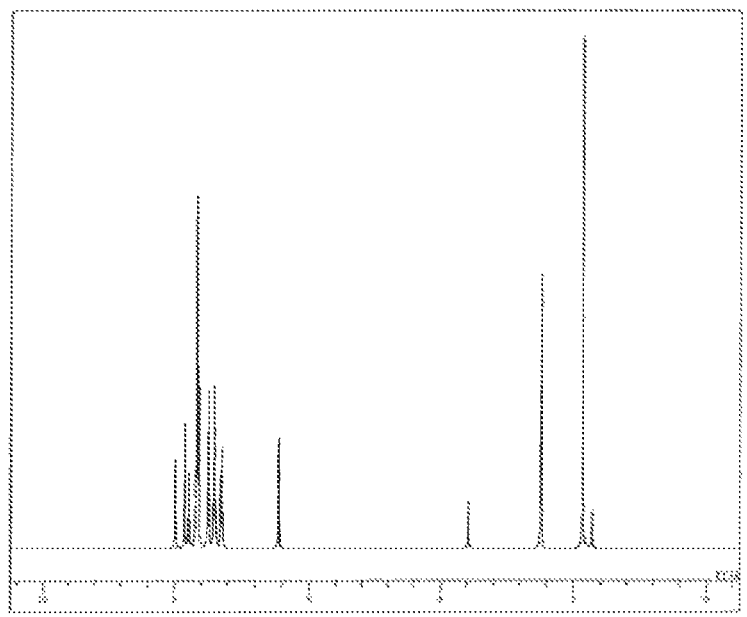
FIG. 1 is a $^1$H-NMR chart of the compound of Example 1 of the present invention (Compound 5).

The compounds having an acridan ring structure of the present invention are novel compounds, and may be synthesized by using, for example, the following method. First, an acridan substituted with an aryl group at the corresponding 10 position is brominated with bromine or N-bromosuccinimide to synthesize a bromo compound substituted at the 2 and/or 7 position (refer to Patent Document 3, for example). This bromo compound can then be used to synthesize the compound having an acridan ring structure in a cross-coupling reaction such as Suzuki coupling (refer to Non-Patent Document 5, for example) with boronic acid or boronate synthesized by reaction with pinacolborane or bis(pinacolato)diboron (refer to Non-Patent Document 4, for example).

Here, the compound having an acridan ring structure synthesized from a monobromo compound brominated at the 2 position can be brominated at the 7 position in the same manner to introduce a substituent at the 7 position in a cross-coupling reaction. Similarly, the compound having an acridan ring structure synthesized from a monobromo compound substituted at the 7 position can be brominated at the 2 position in the same manner to introduce a substituent at the 2 position in a cross-coupling reaction.

Further, the compound having an acridan ring structure may be synthesized to include substituents at different positions by the cross-coupling reaction of an acridan substituted with an aryl group at the 10 position after introducing a bromo group at positions other than the 2 position and the 7 position of the acridan by bromination.

The following presents specific examples of preferred compounds among the compounds of general formula (1) having an acridan ring structure. The present invention, however, is not restricted to these compounds.

[Chemical Formula 5]

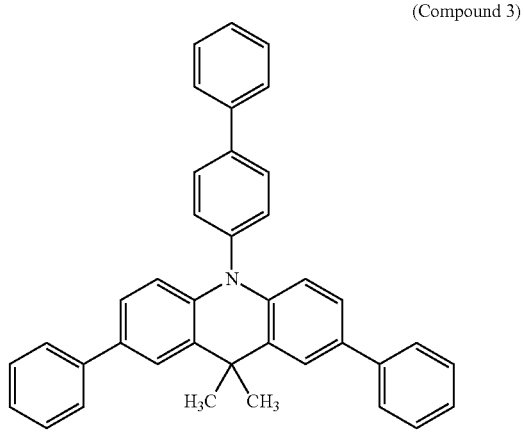

(Compound 3)

[Chemical Formula 6]

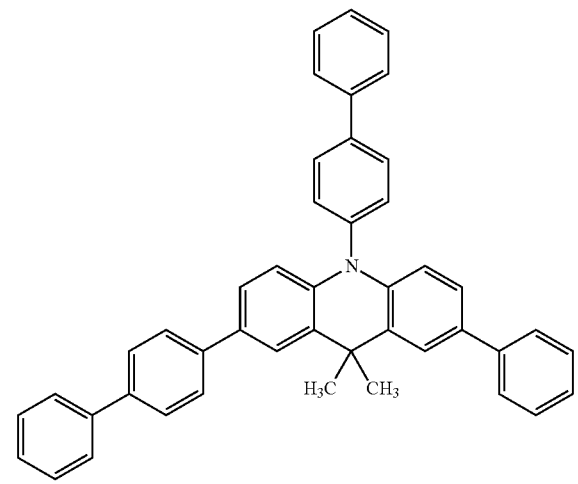

(Compound 4)

[Chemical Formula 7]
(Compound 5)
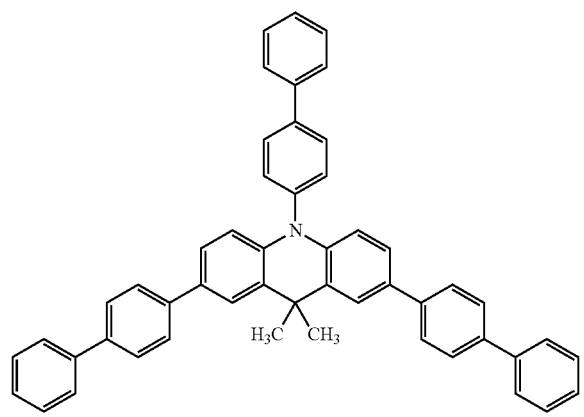
[Chemical Formula 8]
(Compound 6)
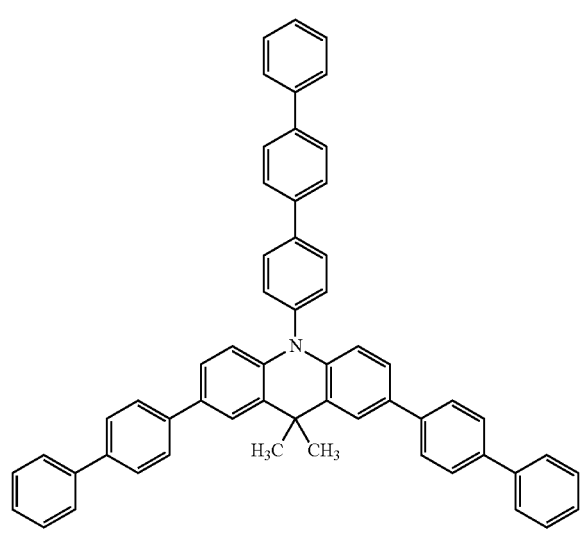
[Chemical Formula 9]
(Compound 7)
[Chemical Formula 10]
(Compound 8)
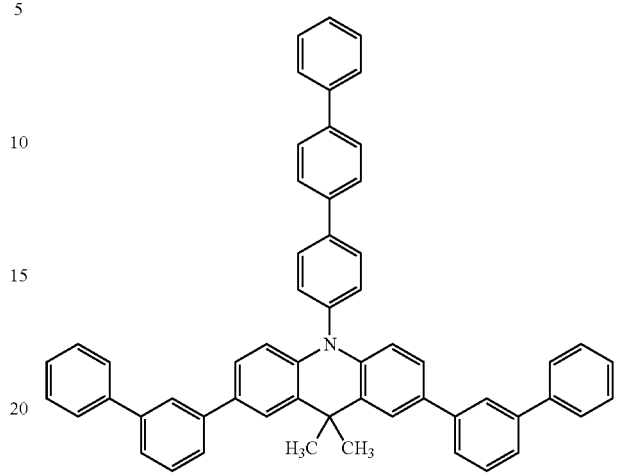
[Chemical Formula 11]
(Compound 9)
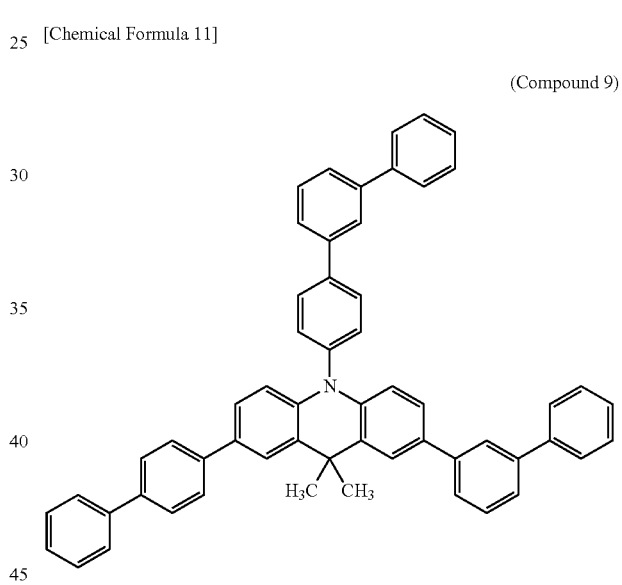
[Chemical Formula 12]
(Compound 10)
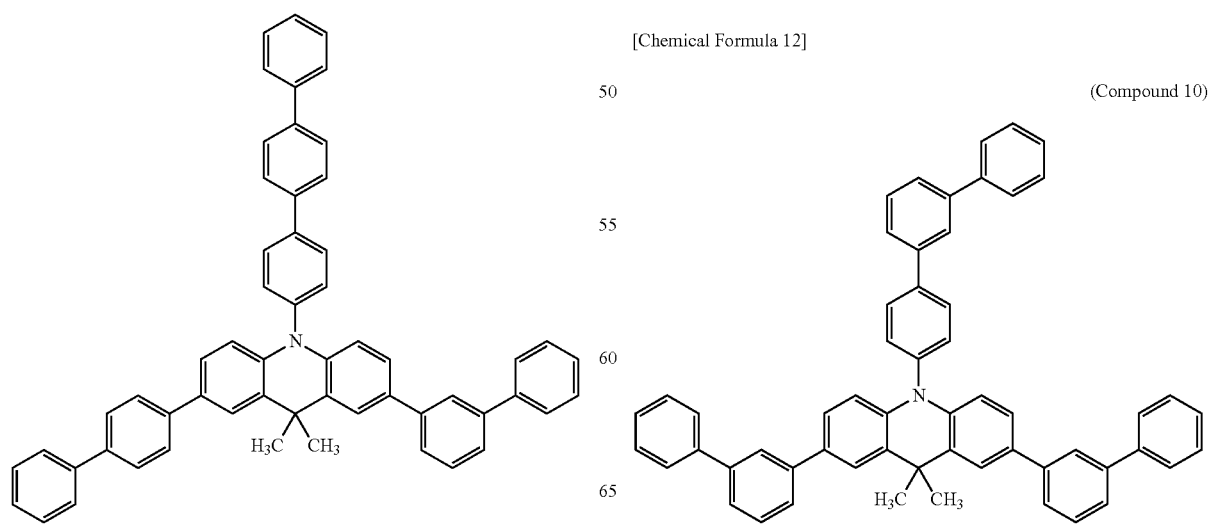

-continued
[Chemical Formula 13]
(Compound 11)
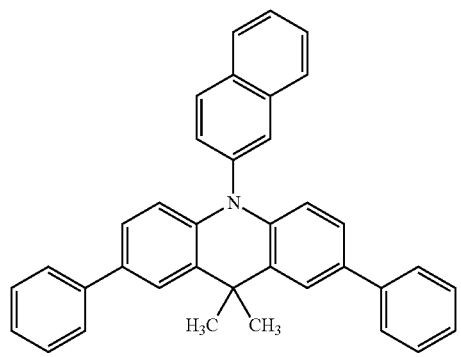
[Chemical Formula 14]
(Compound 12)
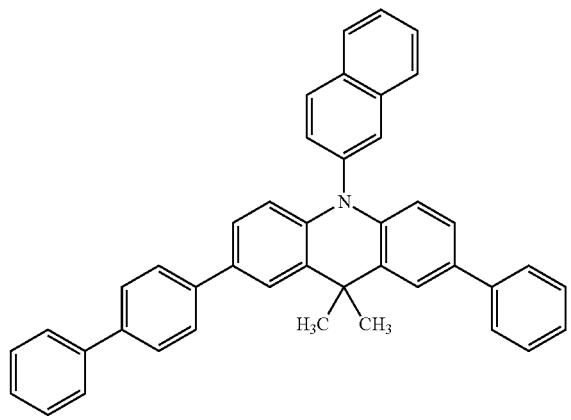
[Chemical Formula 15]
(Compound 13)
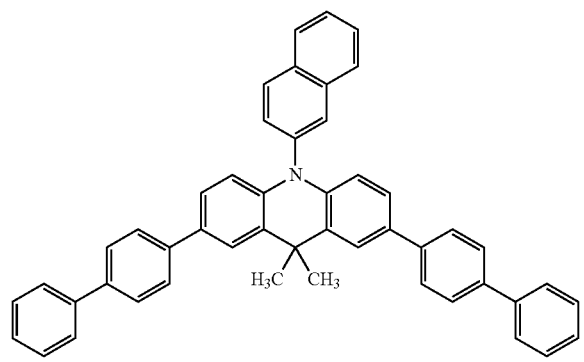
-continued
[Chemical Formula 16]
(Compound 14)
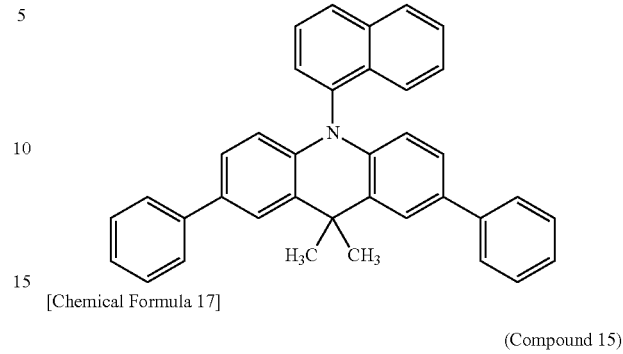
[Chemical Formula 17]
(Compound 15)
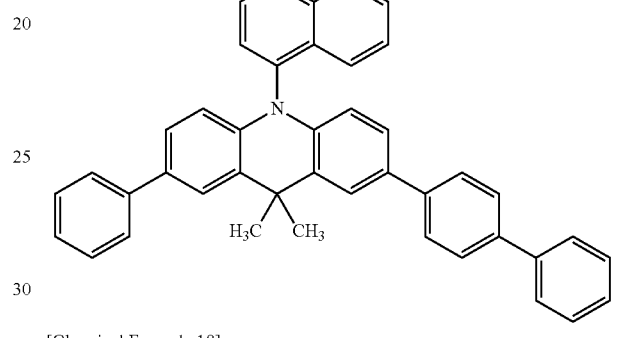
[Chemical Formula 18]
(Compound 16)
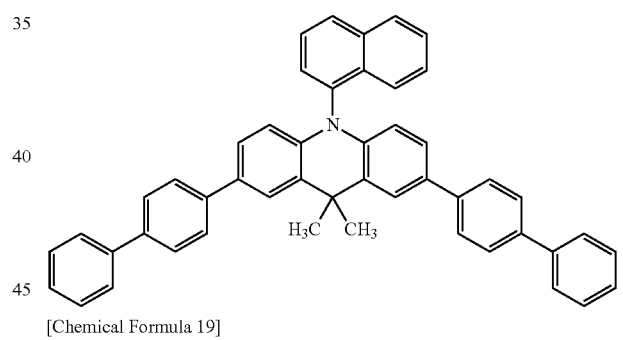
[Chemical Formula 19]
(Compound 17)
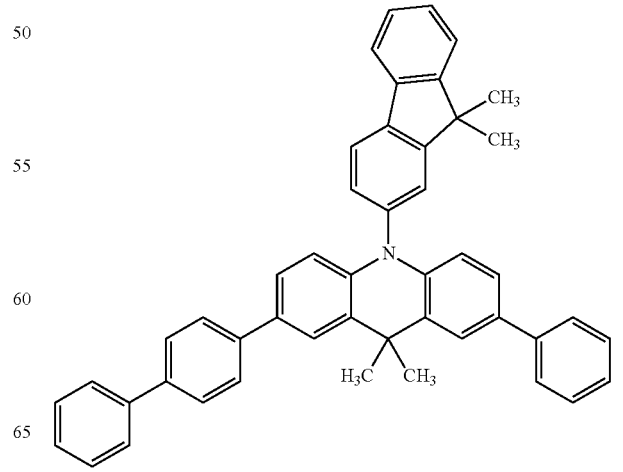

-continued
[Chemical Formula 20]
(Compound 18)
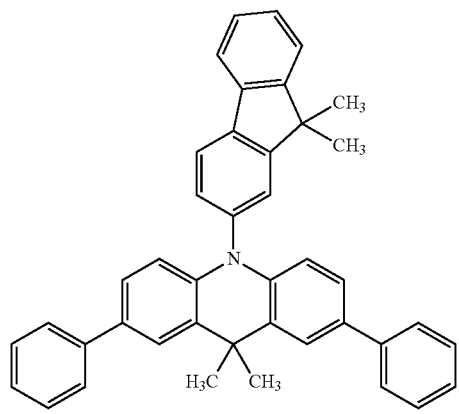
[Chemical Formula 21]
(Compound 19)
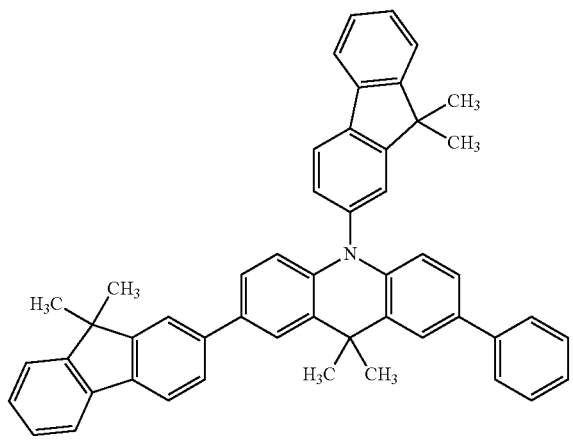
[Chemical Formula 22]
(Compound 20)
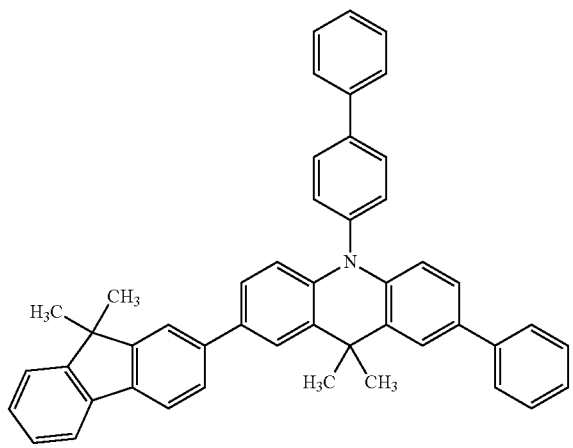
-continued
[Chemical Formula 23]
(Compound 21)
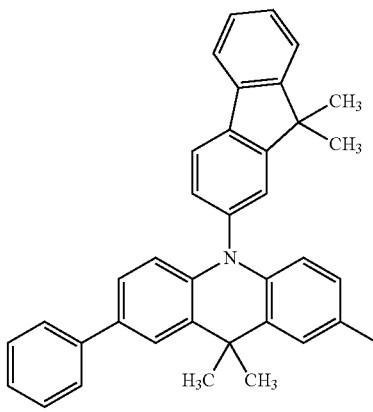
[Chemical Formula 24]
(Compound 22)
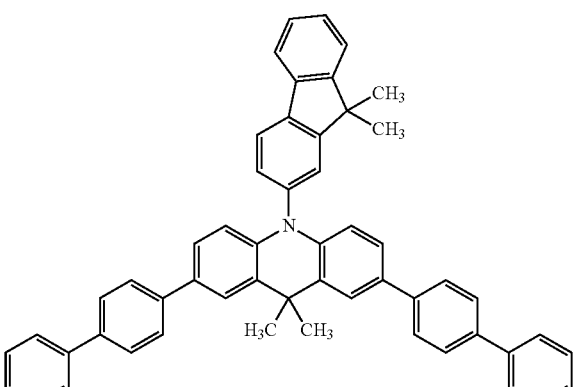
[Chemical Formula 25]
(Compound 23)
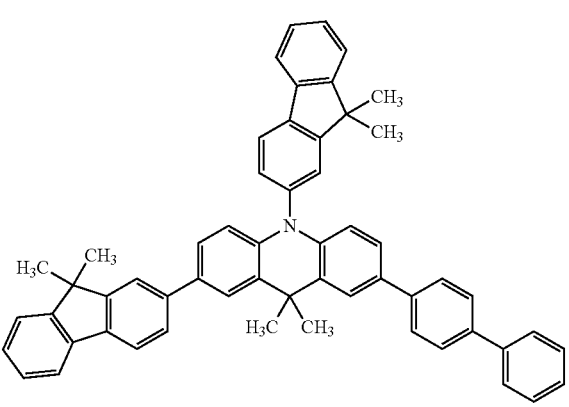

-continued
[Chemical Formula 26]
(Compound 24)
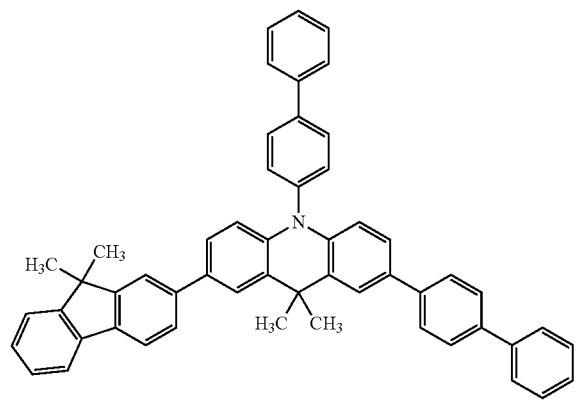
[Chemical Formula 27]
(Compound 25)
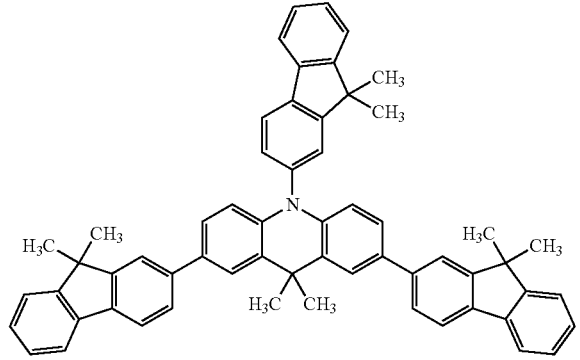
[Chemical Formula 28]
(Compound 26)
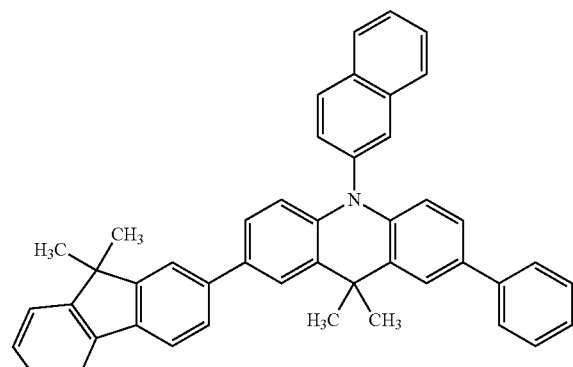
-continued
[Chemical Formula 29]
(Compound 27)
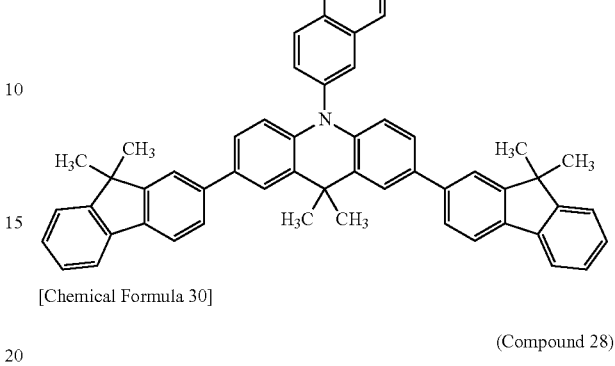
[Chemical Formula 30]
(Compound 28)
[Chemical Formula 31]
(Compound 29)
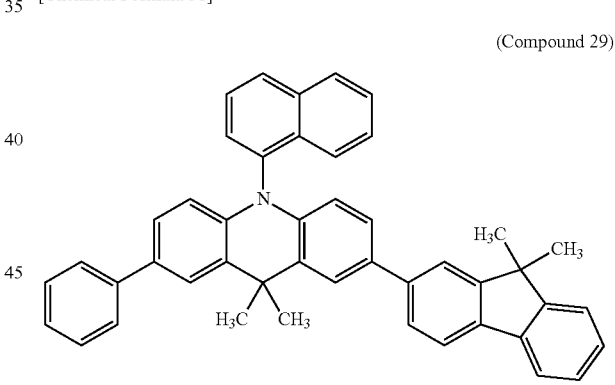
[Chemical Formula 32]
(Compound 30)
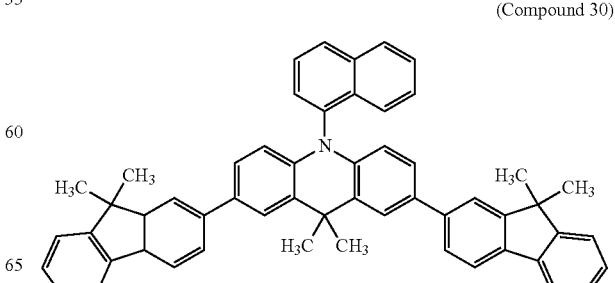

[Chemical Formula 33]
(Compound 31)
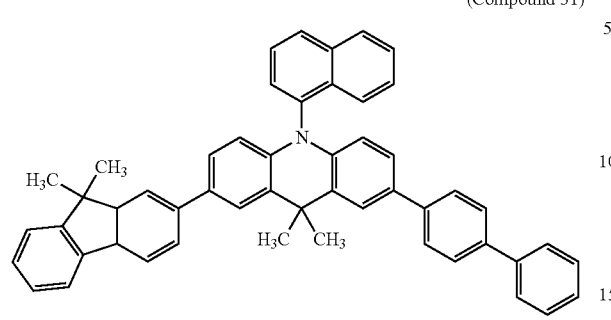
[Chemical Formula 34]
(Compound 32)
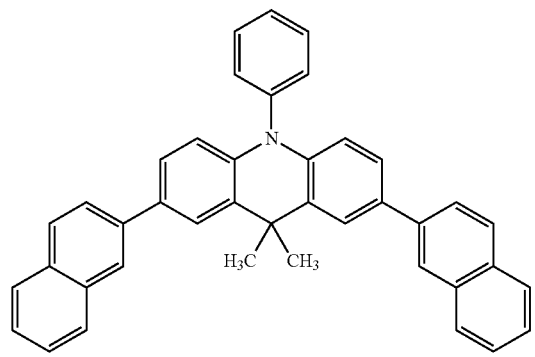
[Chemical Formula 35]
(Compound 33)
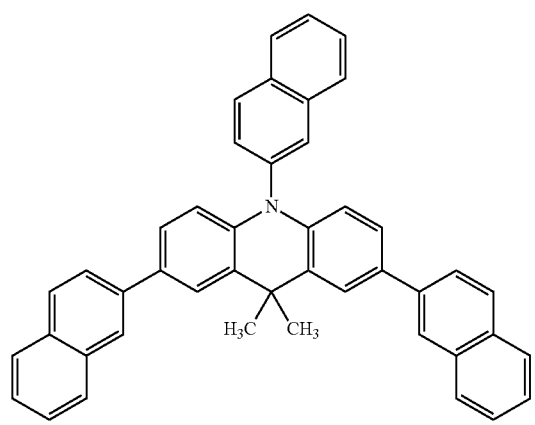
[Chemical Formula 36]
(Compound 34)
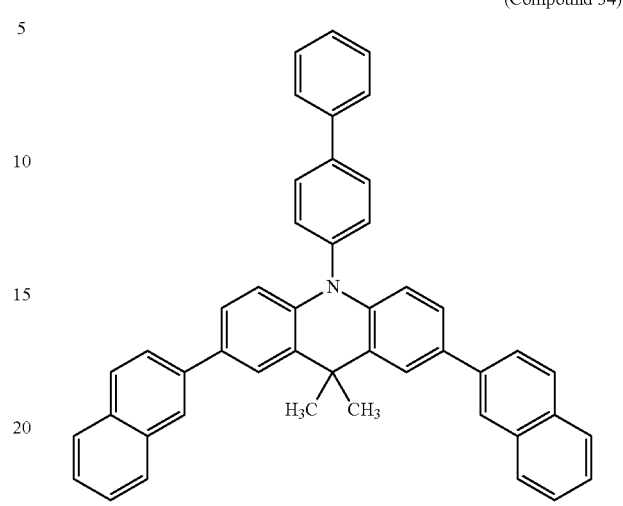
[Chemical Formula 37]
(Compound 35)
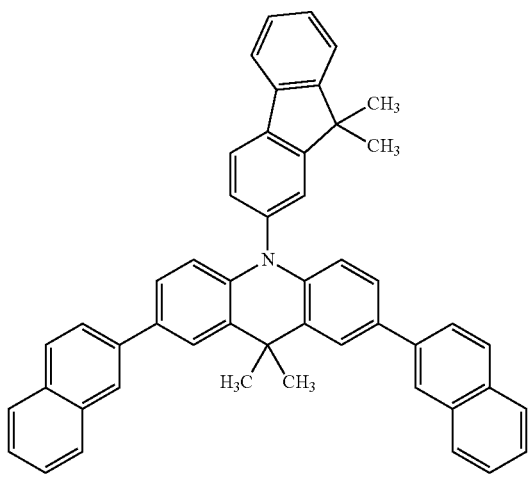
[Chemical Formula 38]
(Compound 36)
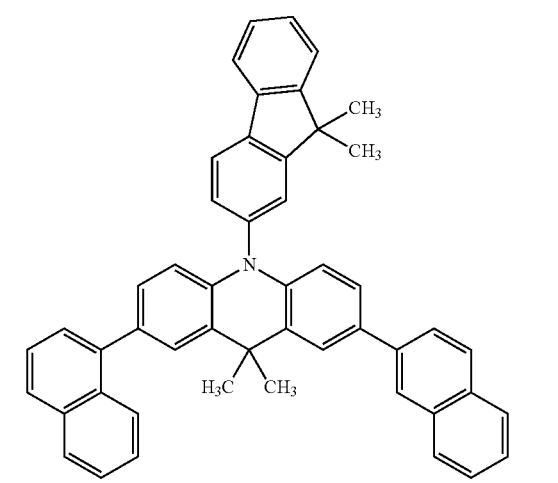

[Chemical Formula 39]
(Compound 37)
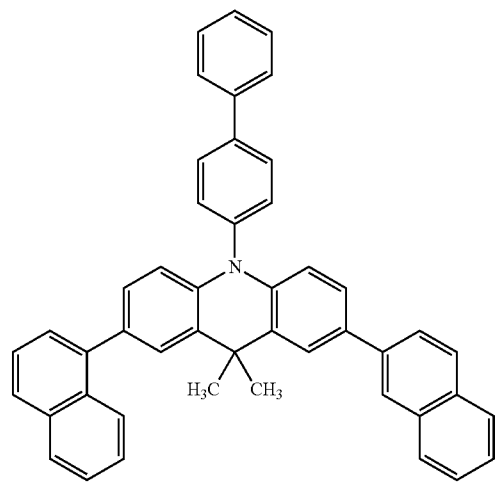
[Chemical Formula 40]
(Compound 38)
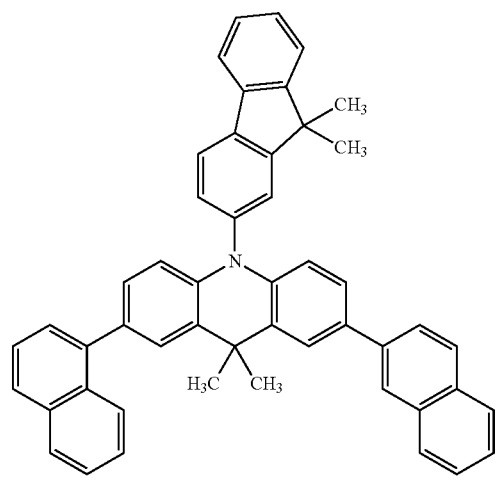
[Chemical Formula 41]
(Compound 39)
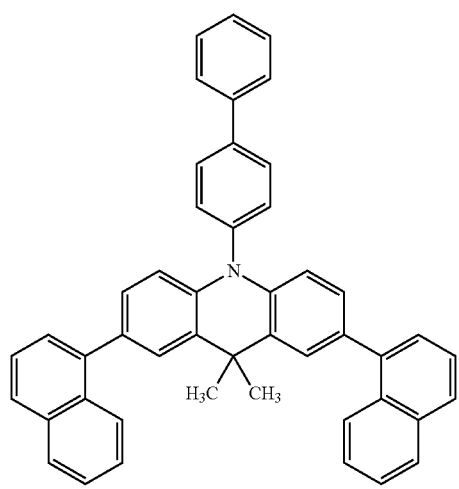
[Chemical Formula 42]
(Compound 40)
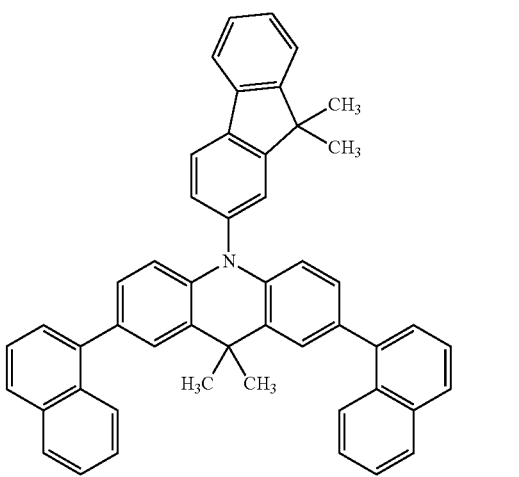
[Chemical Formula 43]
(Compound 41)
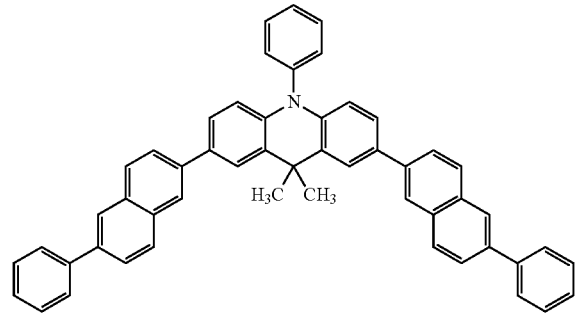
[Chemical Formula 44]
(Compound 42)
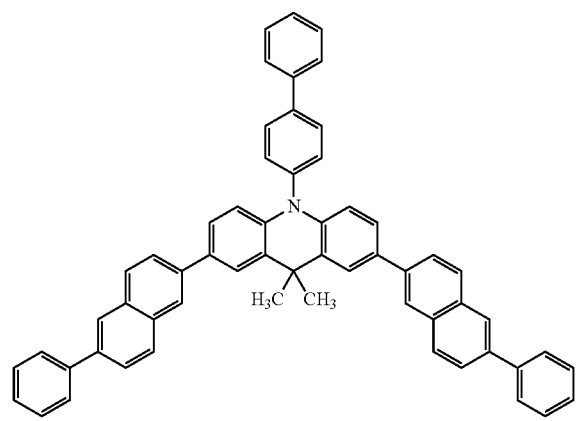

[Chemical Formula 45]
(Compound 43)
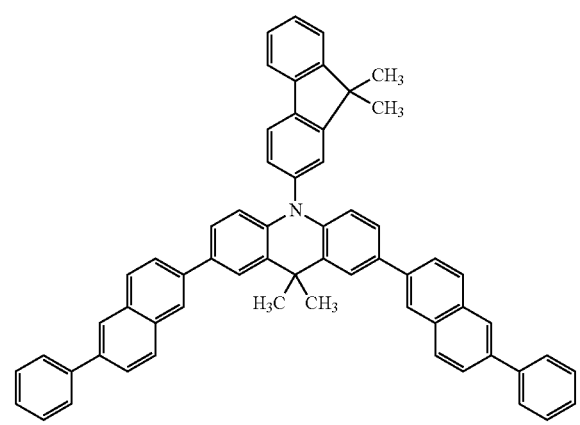
[Chemical Formula 46]
(Compound 44)
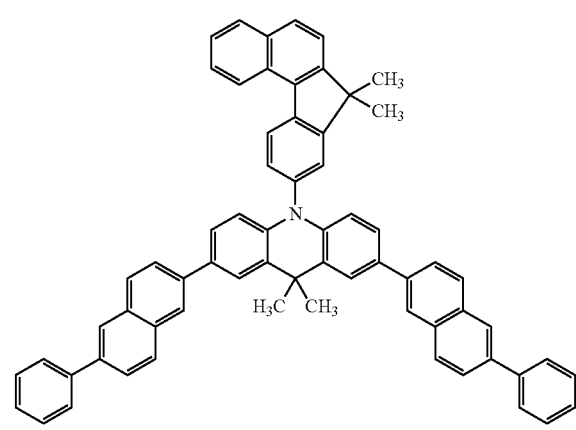
[Chemical Formula 47]
(Compound 45)
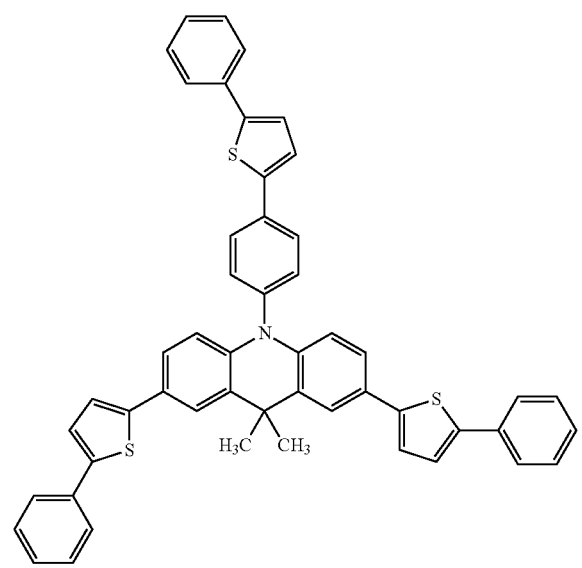
[Chemical Formula 48]
(Compound 46)
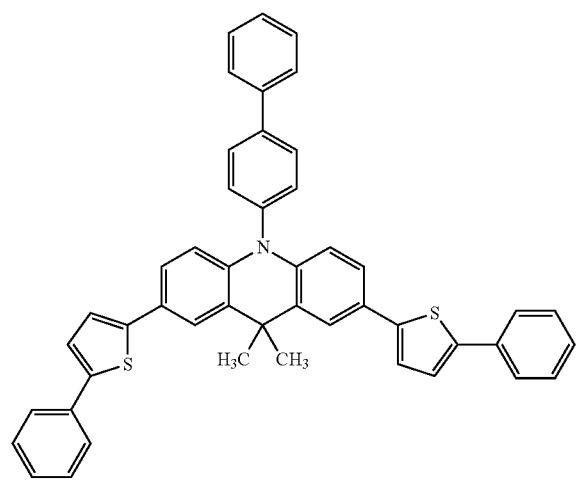
[Chemical Formula 49]
(Compound 47)
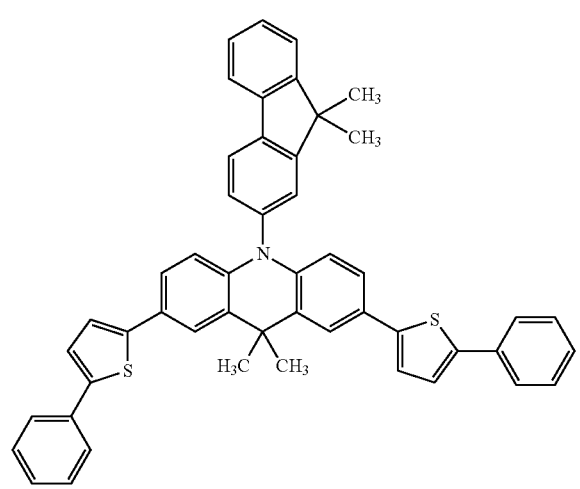
[Chemical Formula 50]
(Compound 48)
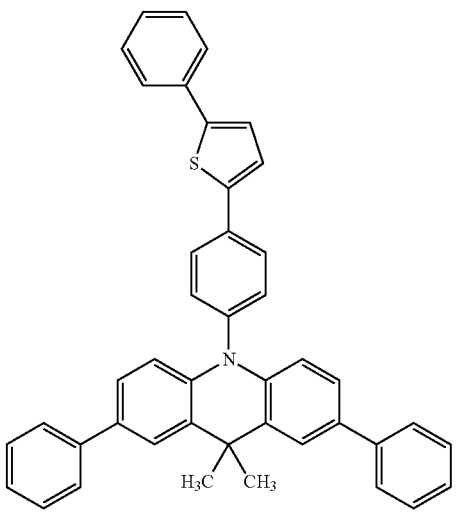

-continued
[Chemical Formula 51]
(Compound 49)
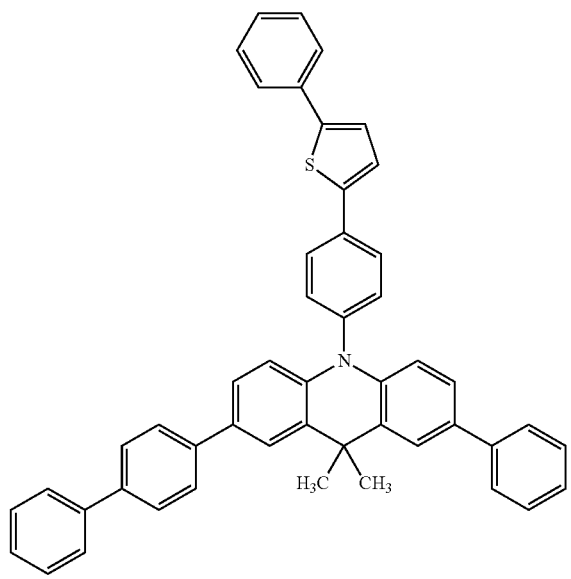
[Chemical Formula 52]
(Compound 50)
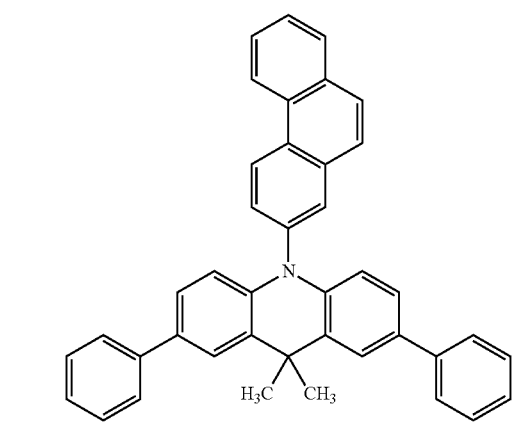
[Chemical Formula 53]
(Compound 51)
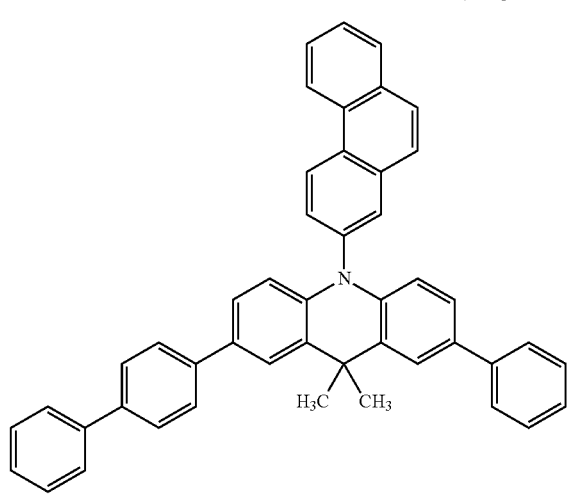
-continued
[Chemical Formula 54]
(Compound 52)
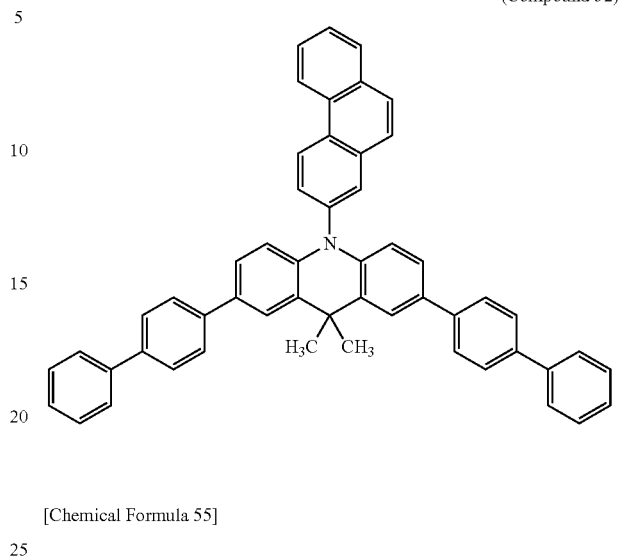
[Chemical Formula 55]
(Compound 53)
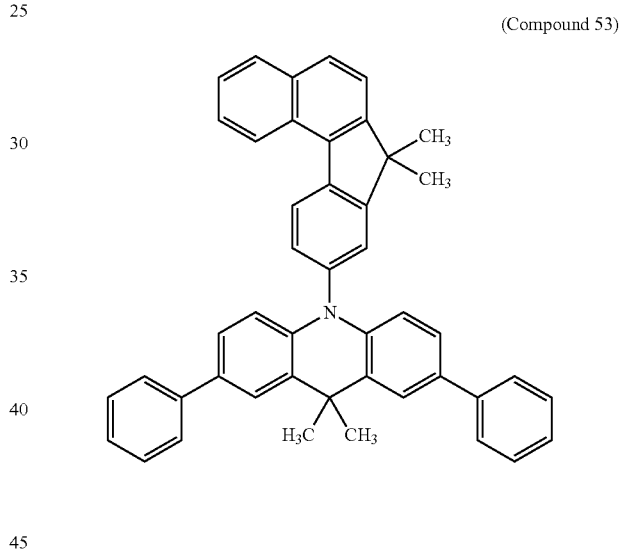
[Chemical Formula 56]
(Compound 54)
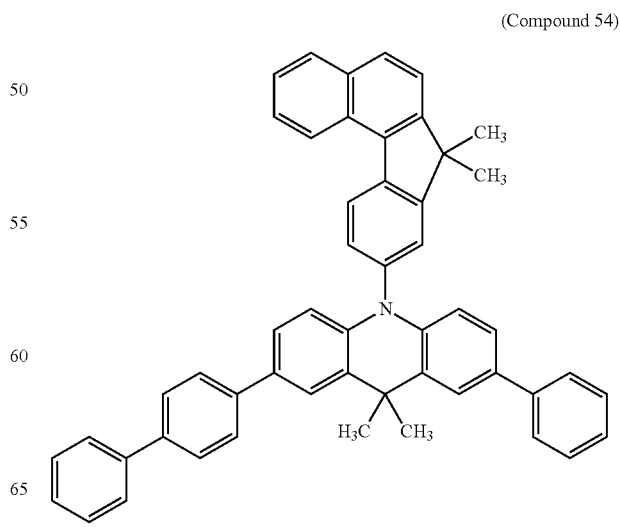

[Chemical Formula 57]
(Compound 55)
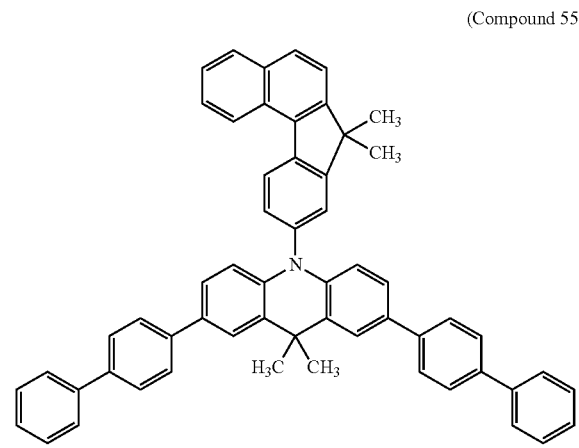
[Chemical Formula 58]
(Compound 56)
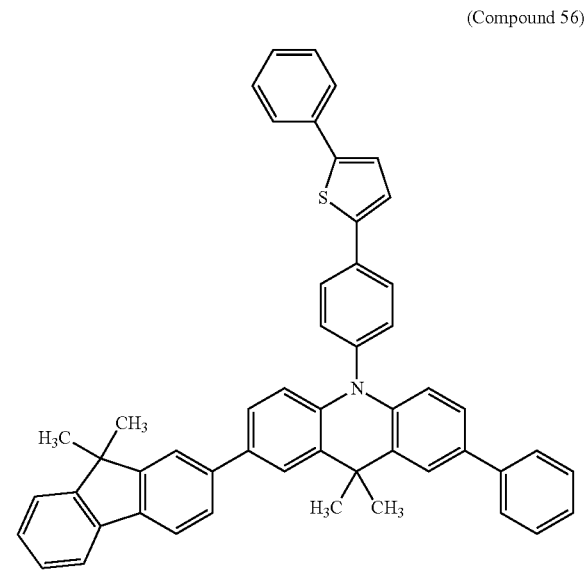
[Chemical Formula 59]
(Compound 57)
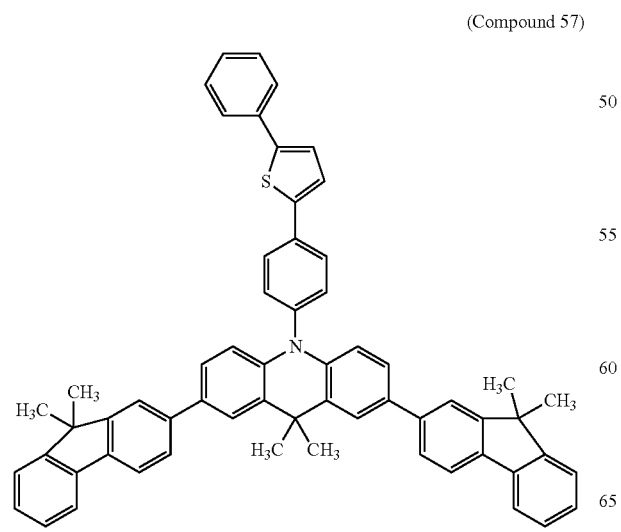
[Chemical Formula 60]
(Compound 58)
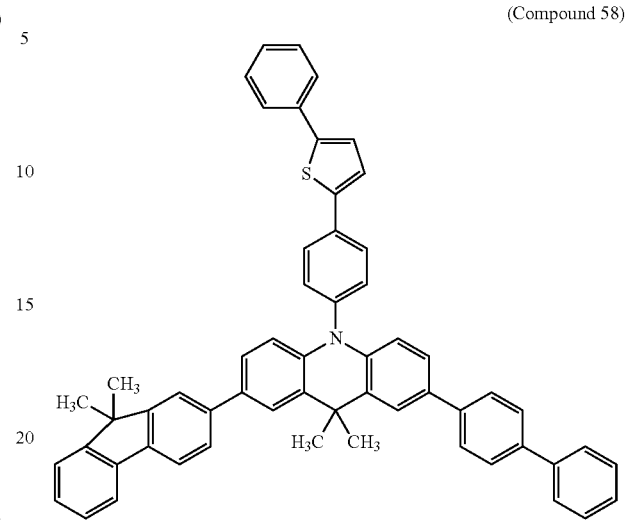
[Chemical Formula 61]
(Compound 59)
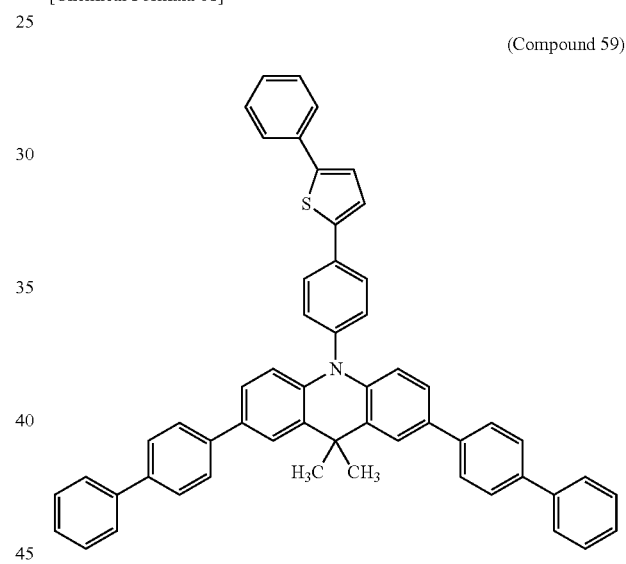
[Chemical Formula 62]
(Compound 60)
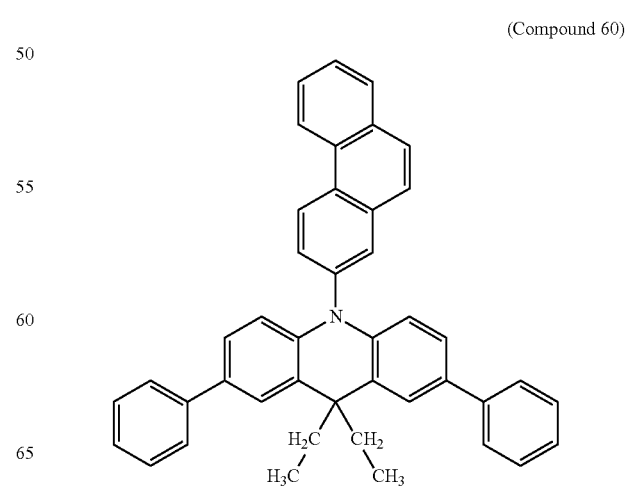

[Chemical Formula 63]
(Compound 61)
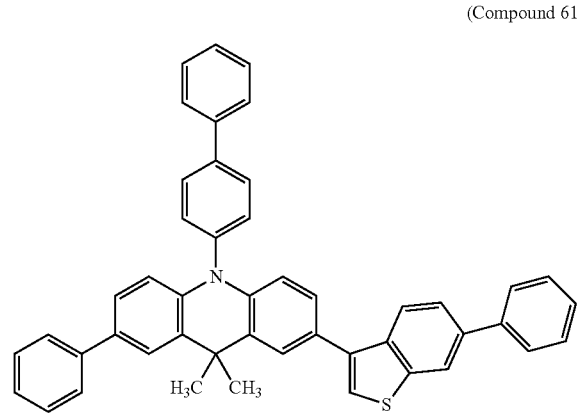
[Chemical Formula 64]
(Compound 62)
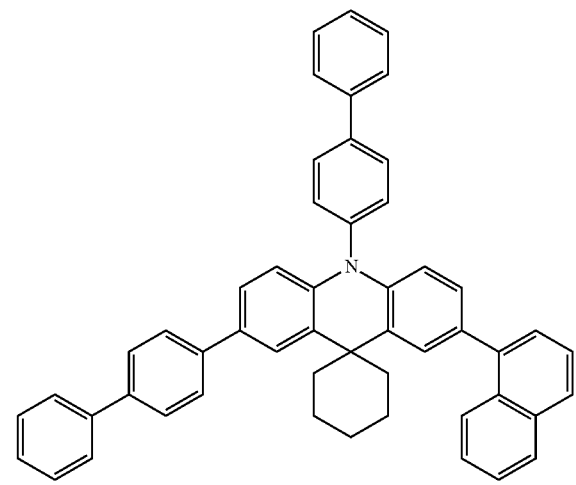
[Chemical Formula 65]
(Compound 63)
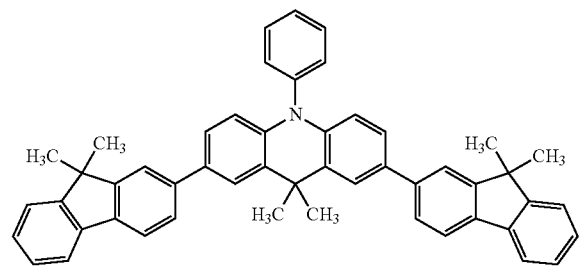
[Chemical Formula 66]
(Compound 64)
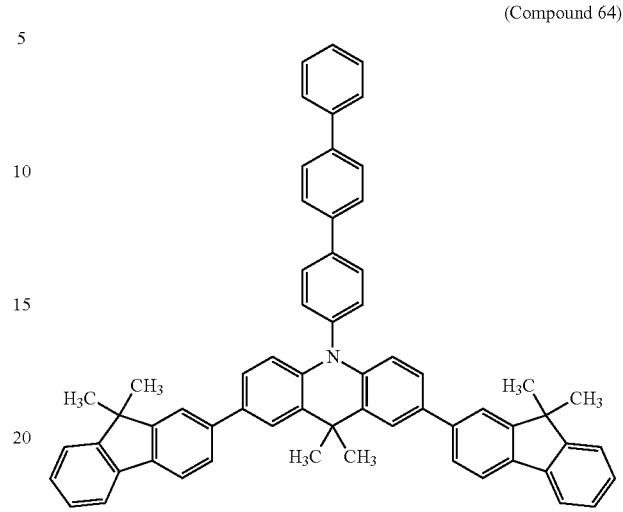
[Chemical Formula 67]
(Compound 65)
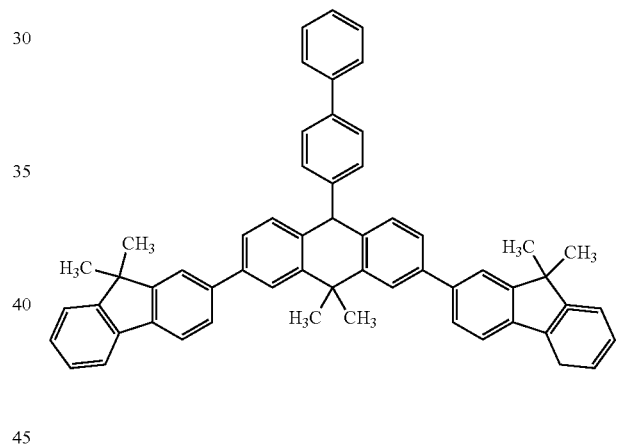
[Chemical Formula 68]
(Compound 66)
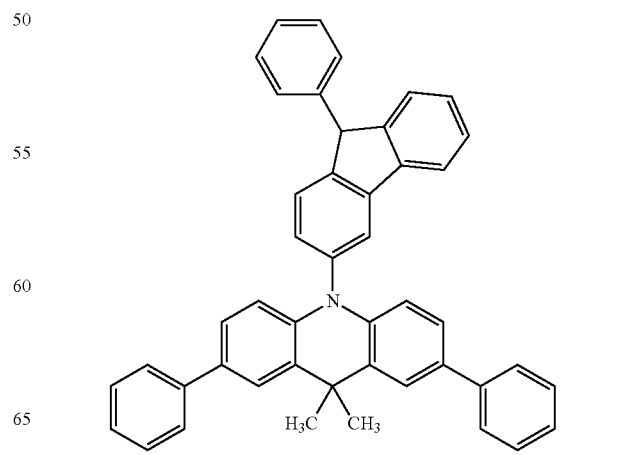

-continued

[Chemical Formula 69]

(Compound 67)

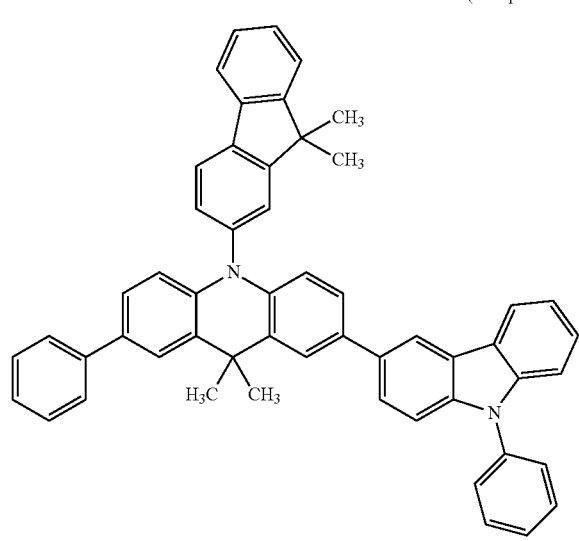

[Chemical Formula 70]

(Compound 68)

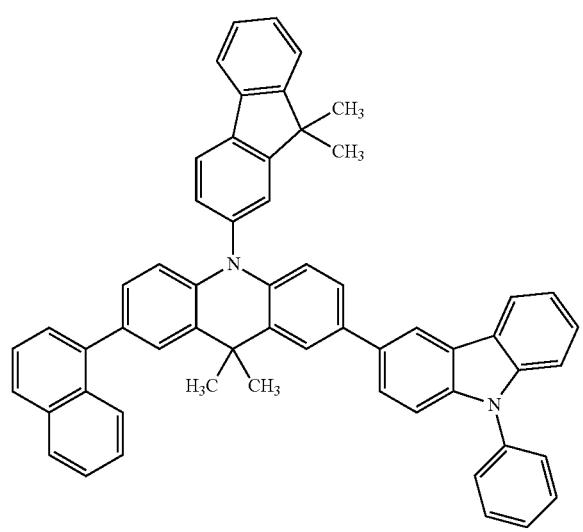

[Chemical Formula 71]

(Compound 69)

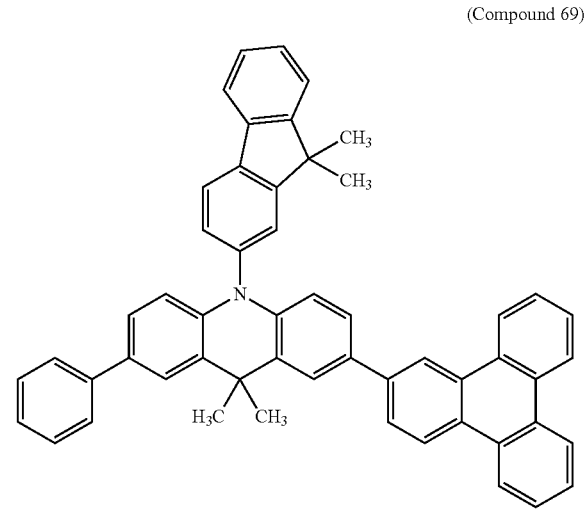

-continued

[Chemical Formula 72]

(Compound 70)

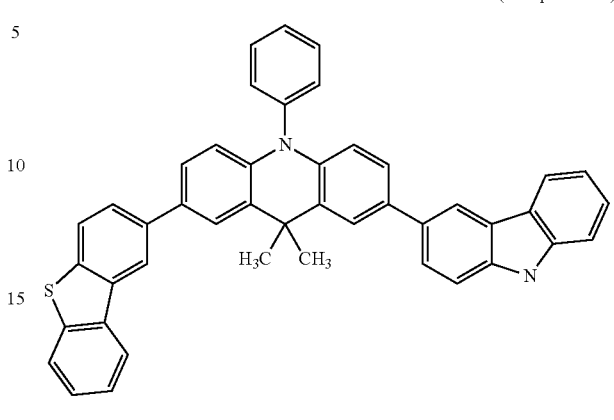

These compounds were purified by methods such as column chromatography, adsorption using, for example, silica gel, activated carbon, or activated clay, and recrystallization or crystallization using a solvent. The compounds were identified by an NMR analysis. A glass transition point (Tg), a melting point, and a work function were measured as material property values. The glass transition point (Tg) can be used as an index of stability in the thin-film state, the melting point as an index of vapor deposition, and the work function as an index of hole transportability.

The glass transition point (Tg) and the melting point were measured by a high-sensitive differential scanning calorimeter (DSC3100S produced by Bruker AXS) using powder.

For the measurement of the work function, a 100 nm-thick thin film was fabricated on an ITO substrate, and an atmosphere photoelectron spectrometer (AC-3 produced by Riken Keiki Co., Ltd.) was used.

The organic EL device of the present invention may have a structure including an anode, a hole transport layer, an electron blocking layer, a light emitting layer, an electron transport layer, and a cathode successively formed on a substrate, optionally with a hole injection layer between the anode and the hole transport layer, or with an electron injection layer between the electron transport layer and the cathode. In such multilayer structures, some of the organic layers may be omitted. For example, the device may be configured to include an anode, a hole transport layer, a light emitting layer, an electron transport layer, and a cathode successively formed on a substrate.

Electrode materials with high work functions such as ITO and gold are used as the anode of the organic EL device of the present invention. The hole injection layer of the organic EL device of the present invention may be made of material such as porphyrin compounds as represented by copper phthalocyanine, starburst-type triphenylamine derivatives, various triphenylamine tetramers, accepting heterocyclic compounds such as hexacyano azatriphenylene, and coating-type polymer materials, in addition to the compounds of general formula (1) having an acridan ring structure of the present invention. These materials may be formed into a thin film by a vapor deposition method or other known methods such as a spin coating method and an inkjet method.

Examples of material used for the hole transport layer of the organic EL device of the present invention can be benzidine derivatives such as N,N'-diphenyl-N,N'-di(m-tolyl)benzidine (hereinafter referred to as TPD), N,N'-diphenyl-N,N'-di(α-naphthyl)benzidine (hereinafter referred to as NPD), and N,N,N',N'-tetrabiphenylylbenzidine; 1,1-bis[4-(di-4-tolylamino)phenyl]cyclohexane (hereinafter referred to as TAPC); and various triphenylamine trimers and tetramers, in addition to the compounds of general formula (1) having an acridan ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (hereinafter referred to as PEDOT)/poly(styrene sulfonate) (hereinafter referred to as PSS). These materials may be formed into a thin-film by a vapor deposition method or other known methods such as a spin coating method and an inkjet method.

Further, material used for the hole injection layer or the hole transport layer may be obtained by p-doping trisbromophenylamine hexachloroantimony or the like into the material commonly used for these layers, or may be, for example, polymer compounds each having a TPD structure as a part of the compound structure.

Examples of material used for the electron blocking layer of the organic EL device of the present invention can be compounds having an electron blocking effect, including, for example, carbazole derivatives such as 4,4',4''-tri(N-carbazolyl)triphenylamine (hereinafter referred to as TCTA), 9,9-bis(4-(carbazol-9-yl)phenyl)fluorene, 1,3-bis(carbazol-9-yl)benzene (hereinafter referred to as mCP), and 2,2-bis(4-carbazol-9-ylphenyl)adamantane (hereinafter referred to as Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the compounds of general formula (1) having an acridan ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may comprise a host material and a dopant material. Examples of the host material can be thiazole derivatives, benzimidazole derivatives, and polydialkyl fluorene derivatives, in addition to the above light-emitting materials and the compounds of general formula (1) having an acridan ring structure of the present invention. Examples of the dopant material can be quinacridone, coumarin, rubrene, perylene, derivatives thereof, benzopyran derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent light-emitting material. Phosphorescent materials as metal complexes of metals such as iridium and platinum may be used as the phosphorescent light-emitting material. Examples of the phosphorescent materials can be green phosphorescent materials such as $Ir(ppy)_3$, blue phosphorescent materials such as FIrpic and $FIr_6$, and red phosphorescent materials such as $Btp_2Ir(acac)$. As the hole injecting and transporting host material, the compounds of general formula (1) having an acridan ring structure of the present invention may be used in addition to carbazole derivatives such as 4,4'-di(N-carbazolyl)biphenyl (hereinafter referred to as CBP), TCTA, and mCP. Compounds such as p-bis(triphenylsilyl)benzene (hereinafter referred to as UGH2) and 2,2',2''-(1,3,5-phenylene)-tris(1-phenyl-1H-benzimidazole) (hereinafter referred to as TPBI) may be used as the electron transporting host material to produce a high-performance organic EL device.

In order to avoid concentration quenching, it is preferable to dope the host material with the phosphorescent light-emitting material by co-evaporation in a range of 1 to 30 weight percent to the whole light emitting layer.

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (hereinafter referred to as BCP), and the metal complexes of quinolinol derivatives such as aluminum(III) bis(2-methyl-8-quinolinate)-4-phenylphenolate (hereinafter referred to as BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron transport layer of the organic EL device of the present invention can be various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to the metal complexes of quinolinol derivatives such as $Alq_3$ and BAlq. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

EXAMPLE 1

Synthesis of 2,7,10-tris(biphenyl-4-yl)-9,9-dimethylacridan (Compound 5)

10-(Biphenyl-4-yl)-2,7-dibromo-9,9-dimethylacridan (3.90 g), 4-biphenylboronic acid (1.64 g), toluene (39 ml), ethanol (10 ml), and a 2 M potassium carbonate aqueous solution (11 ml) were added to a reaction vessel in a nitrogen atmosphere, and aerated with nitrogen gas for 30 minutes under ultrasonic irradiation. The mixture was heated after adding tetrakis(triphenylphosphine)palladium (0.17 g), and stirred at 68° C. for 6.5 hours. The mixture was allowed to cool to room temperature, and methanol (50 ml) was added. The precipitated crude product was then collected by filtration. The crude product was dissolved in toluene (100 ml), and purified by adsorption with a silica gel (10 g). After being concentrated under reduced pressure, the product was washed with methanol (50 ml), and precipitated into crystals with a toluene/methanol mixed solvent. After recrystallization with 1,2-dichlorobenzene and the subsequent crystallization with a 1,2-dichlorobenzene/ethyl acetate mixed solvent, the product was washed under reflux with methanol to obtain a white powder of 2,7,10-tris(biphenyl-4-yl)-9,9-dimethylacridan (Compound 5; 1.77 g; yield 35%).

The structure of the product white powder was identified by NMR. The $^1$H-NMR measurement result is shown in FIG. 1.

$^1$H-NMR (THF-$d_8$) detected 39 hydrogen signals, as follows. δ (ppm)=7.99 (2H), 7.85 (2H), 7.79 (2H), 7.69-7.64 (12H), 7.49 (4H), 7.42-7.37 (5H), 7.31-7.28 (4H), 6.45 (2H), 1.86 (6H).

EXAMPLE 2

Synthesis of 10-(biphenyl-4-yl)-2,7-bis(9,9-dimethyl-9H-fluoren-2-yl)-9,9-dimethylacridan (Compound 65)

10-(Biphenyl-4-yl)-2,7-dibromo-9,9-dimethylacridan (3.48 g), 2-(9,9-dimethyl-9H-fluoren-2-yl)-4,4,5,5-tetramethyl-[1,3,2]dioxaborolane (4.52 g), toluene (52 ml), ethanol (13 ml), and a 2 M potassium carbonate aqueous solution (10 ml) were added to a reaction vessel in a nitrogen atmosphere, and aerated with nitrogen gas for 30 minutes under ultrasonic irradiation. The mixture was heated after adding tetrakis(triphenylphosphine)palladium (0.23 g), and stirred at 68° C. for 6 hours. The mixture was allowed to cool to room temperature, and the organic layer was collected by separation. The organic layer was dried over magnesium sulfate, and concentrated under reduced pressure to obtain a brown crude product. The crude product was purified by column chromatography (support: silica gel, eluent: hexane/toluene), and washed with methanol and then with diisopropyl ether. The washing procedure was repeated to obtain a white powder of 10-(biphenyl-4-yl)-2,7-bis(9,9-dimethyl-9H-fluoren-2-yl)-9,9-dimethylacridan (Compound 65; 2.70 g; yield 54%).

Figure 2:
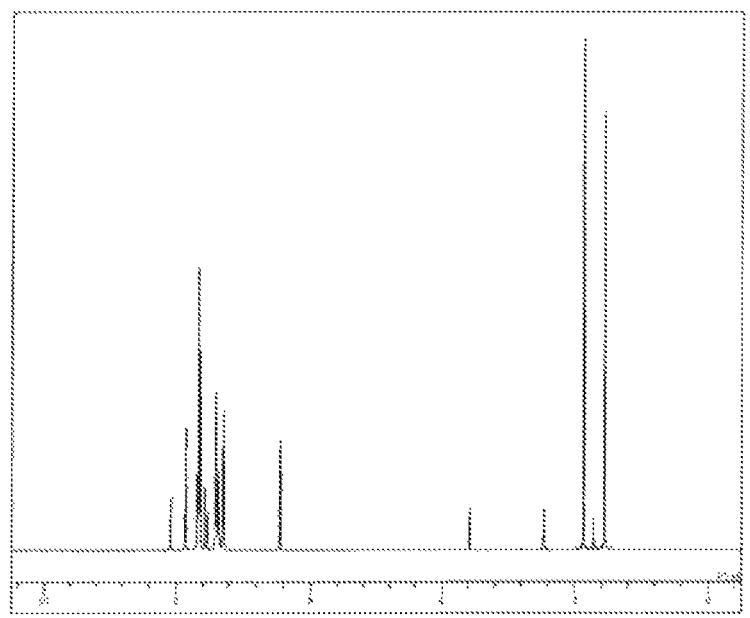
FIG. 2 is a $^1$H-NMR chart of the compound of Example 2 of the present invention (Compound 65).

The structure of the product white powder was identified by NMR. The $^1$H-NMR measurement result is shown in FIG. 2.

$^1$H-NMR (THF-$d_8$) detected 47 hydrogen signals, as follows. δ (ppm)=8.00 (2H), 7.84 (2H), 7.80-7.73 (6H), 7.67 (2H), 7.56 (2H), 7.51-7.49 (4H), 7.45 (2H), 7.38 (1H), 7.31-7.24 (6H), 6.46 (2H), 1.87 (6H), 1.52 (12H).

EXAMPLE 3

Synthesis of 2,7-bis(biphenyl-4-yl)-10-(9,9-dimethyl-9H-fluoren-2-yl)-9,9-dimethylacridan (Compound 22)

10-(9,9-Dimethyl-9H-fluoren-2-yl)-2,7-dibromo-9,9-dimethylacridan (2.51 g), 4-biphenylboronic acid (1.85 g), toluene (25 ml), ethanol (6 ml), and a 2 M potassium carbonate aqueous solution (7 ml) were added to a reaction vessel in a nitrogen atmosphere, and aerated with nitrogen gas for 30 minutes under ultrasonic irradiation. The mixture was heated after adding tetrakis(triphenylphosphine)palladium (0.10 g), and stirred at 68° C. for 3 hours. The mixture was allowed to cool to room temperature, and the organic layer was collected by separation. The organic layer was dried over magnesium sulfate, and concentrated under reduced pressure to obtain a brown crude product. The crude product was purified by column chromatography (support: silica gel, eluent: hexane/toluene), and washed under reflux with diisopropyl ether to obtain a white powder of 2,7-bis(biphenyl-4-yl)-10-(9,9-dimethyl-9H-fluoren-2-yl)-9,9-dimethylacridan (Compound 22; 2.02 g; yield 64%).

Figure 3:
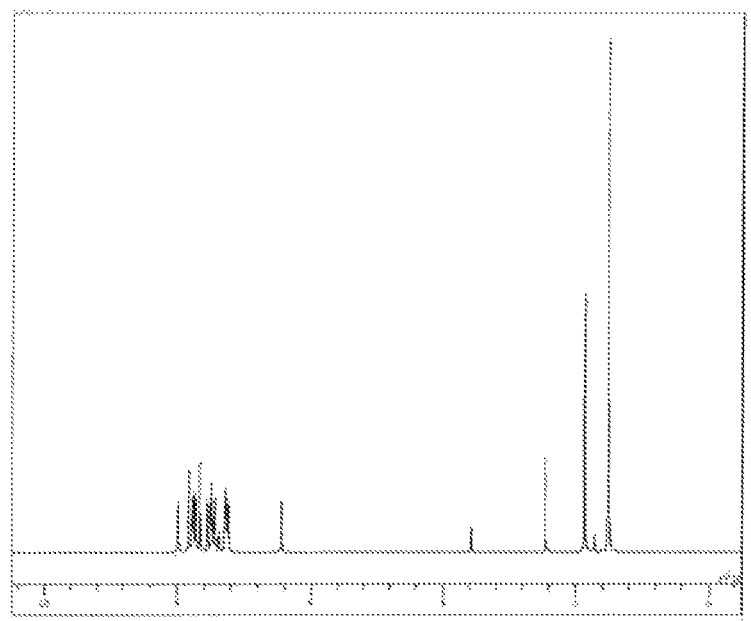
FIG. 3 is a $^1$H-NMR chart of the compound of Example 3 of the present invention (Compound 22).

The structure of the product white powder was identified by NMR. The $^1$H-NMR measurement result is shown in FIG. 3.

$^1$H-NMR (THF-$d_8$) detected 43 hydrogen signals, as follows. δ (ppm)=8.09 (1H), 7.88-7.86 (3H), 7.69-7.64 (12H), 7.57 (1H), 7.53 (1H), 7.42-7.34 (7H), 7.30-7.28 (4H), 6.45 (2H), 1.87 (6H), 1.56 (6H).

EXAMPLE 4

Synthesis of 2,10-bis(biphenyl-4-yl)-9,9-dimethyl-7-phenylacridan (Compound 4)

10-(Biphenyl-4-yl)-2-bromo-9,9-dimethyl-7-phenylacridan (13.00 g), 4-biphenylboronic acid (5.73 g), toluene (195 ml), ethanol (50 ml), and a 2 M potassium carbonate aqueous solution (19 ml) were added to a reaction vessel in a nitrogen atmosphere, and aerated with nitrogen gas for 30 minutes under ultrasonic irradiation. The mixture was heated after adding tetrakis(triphenylphosphine)palladium (0.58 g), and stirred at 68° C. for 4 hours. The mixture was allowed to cool to room temperature, and the organic layer was collected by separation. The organic layer was washed with water (100 ml), and concentrated under reduced pressure. The concentrate was dissolved by adding toluene (445 ml), and purified by adsorption with a silica gel. The resulting product was concentrated under reduced pressure, and crystallized with methanol (300 ml) to obtain a crude product (12.1 g). The crude product was purified by column chromatography (support: silica gel, eluent: toluene) to obtain a white powder of 2,10-bis(biphenyl-4-yl)-9,9-dimethyl-7-phenylacridan (Compound 4; 14.8 g: yield 100%).

Figure 4:
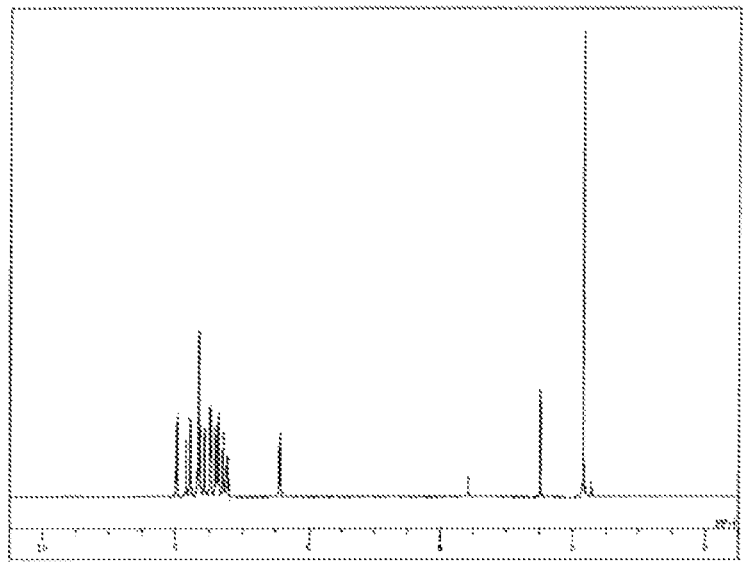
FIG. 4 is a $^1$H-NMR chart of the compound of Example 4 of the present invention (Compound 4).

The structure of the product white powder was identified by NMR. The ¹H-NMR measurement result is shown in FIG. 4.

¹H-NMR (THF-d$_8$) detected 35 hydrogen signals, as follows. δ (ppm)=7.99 (2H), 7.85 (1H), 7.78 (3H), 7.66 (6H), 7.58 (2H), 7.49 (4H), 7.39 (5H), 7.30 (2H), 7.24 (2H), 6.44 (2H), 1.84 (6H).

EXAMPLE 5

Synthesis of 9,9-dimethyl-2,7-diphenyl-10-(9-phenyl-9H-carbazol-3-yl)acridan (Compound 66)

2,7-Dibromo-9,9-dimethylacridan (10.00 g), phenylboronic acid (7.34 g), toluene (150 ml), and a 2 M potassium carbonate aqueous solution (40 ml) were added to a reaction vessel in a nitrogen atmosphere, and aerated with nitrogen gas for 30 minutes under ultrasonic irradiation. The mixture was heated after adding tetrakis(triphenylphosphine)palladium (0.63 g), and stirred at 78° C. for 4.5 hours. The mixture was further stirred at 78° C. for 2 hours after adding phenylboronic acid (0.34 g). After allowing the mixture to cool to room temperature, the insoluble matter was removed by filtration, and the organic layer was collected by separation. The organic layer was dried over magnesium sulfate, and concentrated under reduced pressure to obtain a brown crude product. The crude product was purified by column chromatography (support: silica gel, eluent: hexane/toluene), and crystallized with hexane to obtain 9,9-dimethyl-2,7-diphenylacridan (5.10 g).

The 9,9-dimethyl-2,7-diphenylacridan (5.03 g), 3-bromo-9-phenyl-9H-carbazole (5.17 g), palladium acetate (0.06 g), tert-butoxy sodium (1.63 g), and toluene (75 ml) were added to a reaction vessel in a nitrogen atmosphere, and aerated with nitrogen gas for 30 minutes under ultrasonic irradiation. The mixture was stirred at 90° C. for 2 hours after adding tri(tert-butyl)phosphine (0.28 ml). Methanol (50 ml), water (50 ml), and toluene (75 ml) were added after allowing the mixture to cool to room temperature, and the organic layer was collected by separation after removing the insoluble matter by filtration. The organic layer was washed twice with water (50 ml), dried over magnesium sulfate, and concentrated under reduced pressure to obtain a brown crude product. The crude product was purified by column chromatography (support: silica gel, eluent: hexane/toluene), crystallized with methanol, and washed under reflux with methanol (50 ml) to obtain a yellow powder of 9,9-dimethyl-2,7-diphenyl-10-(9-phenyl-9H-carbazol-3-yl)acridan (Compound 66; 5.78 g; yield 69%).

Figure 5:
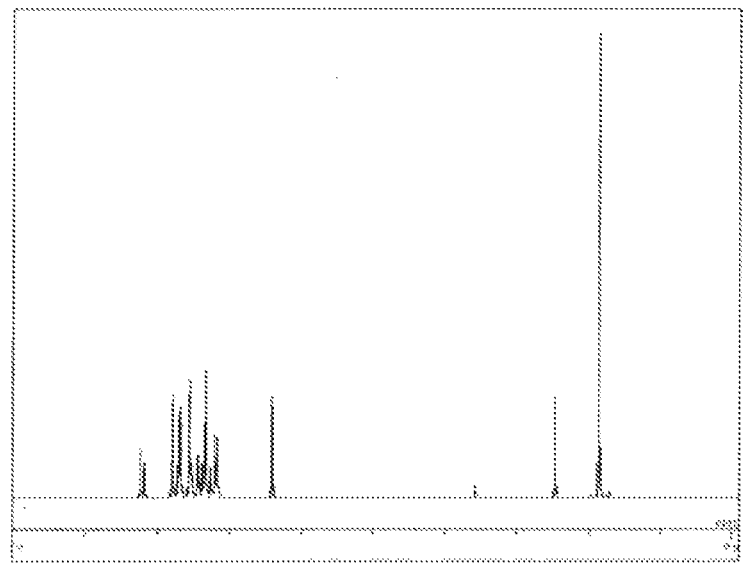
FIG. 5 is a $^1$H-NMR chart of the compound of Example 5 of the present invention (Compound 66).

The structure of the product yellow powder was identified by NMR. The ¹H-NMR measurement result is shown in FIG. 5.

¹H-NMR (THF-d$_8$) detected 34 hydrogen signals, as follows. δ (ppm)=8.21 (2H), 7.78 (2H), 7.72-7.68 (5H), 7.58-7.17 (17H), 6.42 (2H), 1.87 (6H).

EXAMPLE 6

Synthesis of 10-(9,9-dimethyl-9H-fluoren-2-yl)-9,9-dimethyl-2-phenyl-7-(9-phenyl-9H-carbazol-3-yl)acridan (Compound 67)

7-Bromo-10-(9,9-dimethyl-9H-fluoren-2-yl)-9,9-dimethyl-2-phenylacridan (2.79 g), 9-phenyl-3-(4,4,5,5-tetramethyl-[1,3,2]dioxabororan-2-yl)-9H-carbazole (3.98 g), toluene (75 ml), ethanol (19 ml), and a 2 M potassium carbonate aqueous solution (6.5 ml) were added to a reaction vessel in a nitrogen atmosphere, and aerated with nitrogen gas for 30 minutes under ultrasonic irradiation. The mixture was heated after adding tetrakis(triphenylphosphine)palladium (0.20 g), and stirred at 72° C. for 5 hours. The mixture was allowed to cool to room temperature, and the organic layer was collected by separation. The organic layer was washed twice with water (50 ml), dried over magnesium sulfate, and concentrated under reduced pressure to obtain a crude product. The crude product was purified by column chromatography (support: silica gel, eluent: hexane/toluene), and crystallized with a toluene/methanol mixed solvent, diisopropyl ether, and then with a THF/methanol mixed solvent. The crystallization procedure was repeated to obtain a white powder of 10-(9,9-dimethyl-9H-fluoren-2-yl)-9,9-dimethyl-2-phenyl-7-(9-phenyl-9H-carbazol-3-yl)acridan (Compound 67; 3.38 g; yield 52%).

Figure 6:
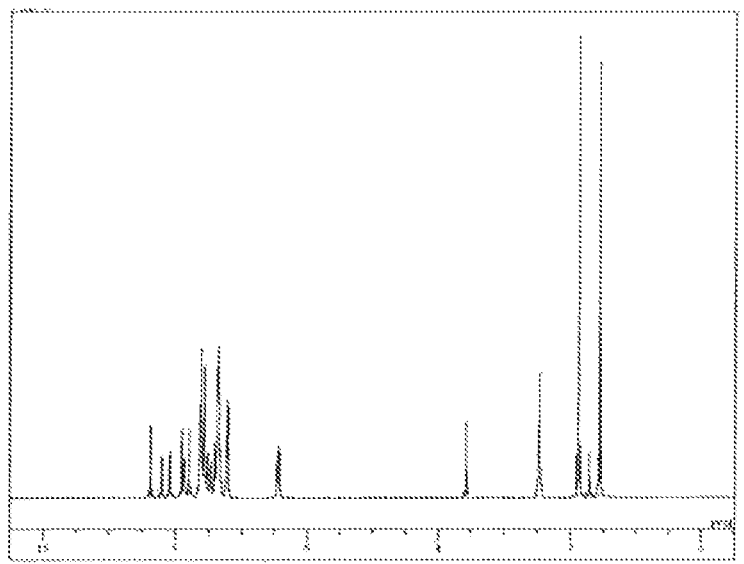
FIG. 6 is a $^1$H-NMR chart of the compound of Example 6 of the present invention (Compound 67).

The structure of the product white powder was identified by NMR. The ¹H-NMR measurement result is shown in FIG. 6.

¹H-NMR (THF-d$_8$) detected 42 hydrogen signals, as follows. δ (ppm)=8.38 (1H), 8.21 (1H), 8.08 (1H), 7.89-7.80 (3H), 7.64-7.32 (19H), 7.24-7.22 (3H), 6.47-6.43 (2H), 1.89 (6H), 1.56 (6H).

EXAMPLE 7

Synthesis of 10-(9,9-dimethyl-9H-fluoren-2-yl)-9,9-dimethyl-2-(naphthalen-1-yl)-7-(9-phenyl-9H-carbazol-3-yl)acridan (Compound 68)

7-Bromo-10-(9,9-dimethyl-9H-fluoren-2-yl)-9,9-dimethyl-2-(naphthalen-1-yl)acridan (5.00 g), 9-phenyl-3-(4,4,5,5-tetramethyl-[1,3,2]dioxabororan-2-yl)-9H-carbazole (3.65 g), toluene (75 ml), ethanol (19 ml), and a 2 M potassium carbonate aqueous solution (6 ml) were added to a reaction vessel in a nitrogen atmosphere, and aerated with nitrogen gas for 30 minutes under ultrasonic irradiation. The mixture was heated after adding tetrakis(triphenylphosphine)palladium (0.19 g), and stirred at 67° C. for 5.5 hours. The mixture was allowed to cool to room temperature, and the organic layer was collected by separation. The organic layer was dried over magnesium sulfate, and concentrated under reduced pressure to obtain a crude product. The crude product was dissolved by adding toluene, and purified by adsorption with a silica gel. The resulting product was purified by column chromatography (support: silica gel, eluent: hexane/toluene), and crystallized with a toluene/hexane mixed solvent, and then with a toluene/diisopropyl ether mixed solvent in a repeated fashion. The resulting product was washed under reflux with methanol to obtain a white powder of 10-(9,9-dimethyl-9H-fluoren-2-yl)-9,9-dimethyl-2-(naphthalen-1-yl)-7-(9-phenyl-9H-carbazol-3-yl)acridan (Compound 68; 3.18 g; yield 50%).

Figure 7:
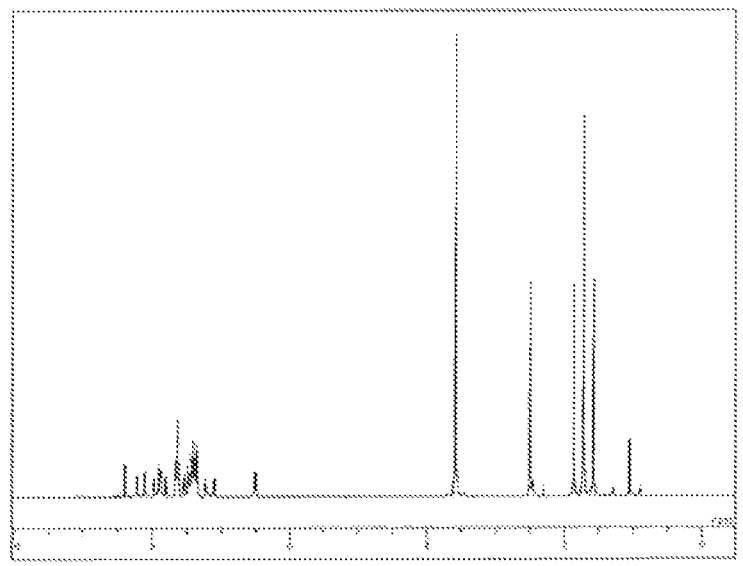
FIG. 7 is a $^1$H-NMR chart of the compound of Example 7 of the present invention (Compound 68).

The structure of the product white powder was identified by NMR. The ¹H-NMR measurement result is shown in FIG. 7.

¹H-NMR (THF-d$_8$) detected 44 hydrogen signals, as follows. δ (ppm)=8.40 (1H), 8.22 (1H), 8.12 (1H), 7.99-7.88 (4H), 7.82 (1H), 7.67-7.64 (7H), 7.55-7.36 (13H), 7.23 (1H), 7.11 (1H), 6.52-6.48 (2H), 1.87 (6H), 1.58 (6H).

EXAMPLE 8

The melting points and the glass transition points of the compounds of the present invention were determined using a high-sensitive differential scanning calorimeter (DSC3100S produced by Bruker AXS).

|  | Melting point | Glass transition point |
| --- | --- | --- |
| Compound of Example 1 of the present invention | 235° C. | 129° C. |
| Compound of Example 2 of the present invention | 168° C. | 148° C. |
| Compound of Example 3 of the present invention | 168° C. | 141° C. |
| Compound of Example 4 of the present invention | 134° C. | 111° C. |
| Compound of Example 5 of the present invention | 219° C. | 132° C. |
| Compound of Example 6 of the present invention | 179° C. | 145° C. |

The compounds of the present invention had glass transition points of 100° C. or more. This indicates that the compounds of the present invention have a stable thin-film state.

EXAMPLE 9

A 100 nm-thick vapor-deposited film was fabricated on an ITO substrate using the compounds of the present invention. The work function was measured using an atmosphere photoelectron spectrometer (AC-3 produced by Riken Keiki Co., Ltd.).

|  | Work function |
| --- | --- |
| Compound of Example 1 of the present invention | 5.57 eV |
| Compound of Example 2 of the present invention | 5.57 eV |
| Compound of Example 3 of the present invention | 5.52 eV |
| Compound of Example 4 of the present invention | 5.63 eV |
| Compound of Example 5 of the present invention | 5.59 eV |
| Compound of Example 6 of the present invention | 5.51 eV |

As shown above, the compounds of the present invention have more desirable energy levels and more desirable hole transportability than common hole transport materials such as NPD and TPD having work functions of 5.4 eV.

EXAMPLE 10

Figure 8:
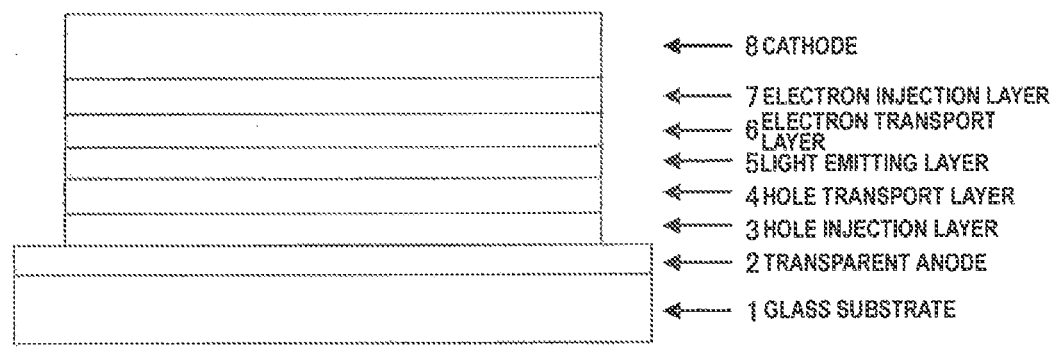
FIG. 8 is a diagram illustrating the configuration of the EL devices of Examples 10 to 12 and Comparative Example 1.

The organic EL device, as illustrated in FIG. 8, was fabricated from a hole injection layer 3, a hole transport layer 4, a light emitting layer 5, an electron transport layer 6, an electron injection layer 7, and a cathode (aluminum electrode) 8 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole injection layer 3 by forming Compound 71 of the structural formula below over the transparent anode 2 in a thickness of 20 nm. The hole transport layer 4 was then formed on the hole injection layer 3 by forming the compound of Example 1 of the present invention (Compound 5) in a thickness of 40 nm. Then, the light emitting layer 5 was formed on the hole transport layer 4 in a thickness of 30 nm by the dual vapor deposition of Compound 72 of the structural formula below and Compound 73 of the structural formula below at a deposition rate ratio of Compound 72:Compound 73=5:95. The electron transport layer 6 was then formed on the light emitting layer 5 by forming Alq$_3$ in a thickness of 30 nm. Then, the electron injection layer 7 was formed on the electron transport layer 6 by forming lithium fluoride in a thickness of 0.5 nm. Finally, the cathode 8 was formed by vapor depositing aluminum in a thickness of 150 nm. The characteristics of the organic EL device thus fabricated were measured in an atmosphere at ordinary temperature.

Table 1 summarizes the results of the emission characteristics measurements performed by applying a DC voltage to the organic EL device fabricated with the compound of Example 1 of the present invention (Compound 5).

[Chemical Formula 73]

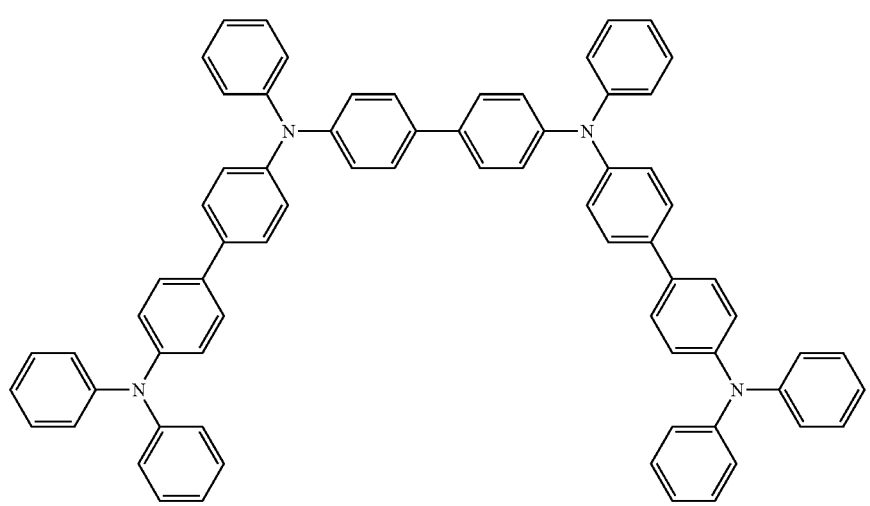

(Compound 71)

[Chemical Formula 74]

(Compound 72)

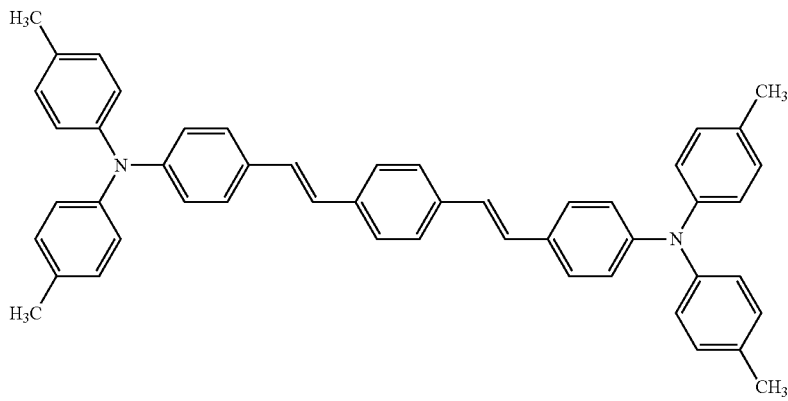

[Chemical Formula 75]

(Compound 73)

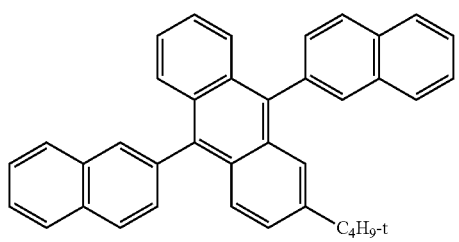

EXAMPLE 11

An organic EL device was fabricated under the same conditions used in Example 10, except that the hole transport layer 4 was formed by forming the compound of Example 3 of the present invention (Compound 22) in a thickness of 40 nm, instead of using the compound of Example 1 of the present invention (Compound 5). The characteristics of the organic EL device thus fabricated were measured in an atmosphere at ordinary temperature. Table 1 summarizes the results of the emission characteristics measurements performed by applying a DC voltage to the organic EL device.

EXAMPLE 12

An organic EL device was fabricated under the same conditions used in Example 10, except that the hole transport layer 4 was formed by forming the compound of Example 6 of the present invention (Compound 67) in a thickness of 40 nm, instead of using the compound of Example 1 of the present invention (Compound 5). The characteristics of the organic EL device thus fabricated were measured in an atmosphere at ordinary temperature. Table 1 summarizes the results of the emission characteristics measurements performed by applying a DC voltage to the organic EL device.

COMPARATIVE EXAMPLE 1

For comparison, an organic EL device was fabricated under the same conditions used in Example 10, except that the hole transport layer 4 was formed by forming Compound 74 of the structural formula below in a thickness of 40 nm, instead of using the compound of Example 1 of the present invention (Compound 5). The characteristics of the organic EL device thus fabricated were measured in an atmosphere at ordinary temperature. Table 1 summarizes the results of the emission characteristics measurements performed by applying a DC voltage to the organic EL device.

[Chemical Formula 76]

(Compound 74)

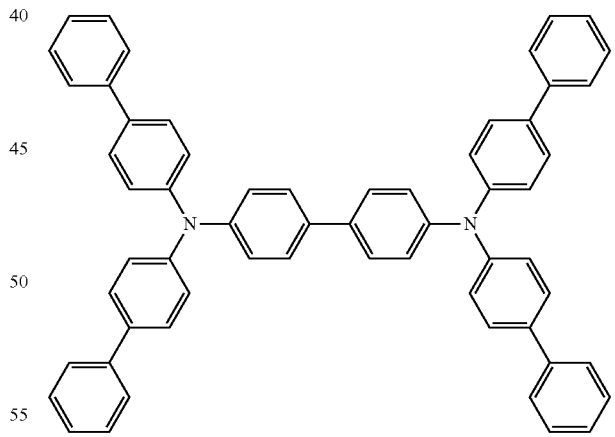

TABLE 1

| | Compound | Voltage [V] (@10 mA/ cm$^2$) | Luminance [cd/m2] (@10 mA/ cm$^2$) | Current efficiency [cd/A] (@10 mA/ cm$^2$) | Power efficiency [lm/W] (@10 mA/ cm$^2$) |
|---|---|---|---|---|---|
| Ex. 10 | Compound 5 | 5.2 | 1050 | 10.5 | 6.07 |
| Ex. 11 | Compound 22 | 4.81 | 1122 | 11.23 | 7.33 |

TABLE 1-continued

| | Compound | Voltage [V] (@10 mA/cm²) | Luminance [cd/m2] (@10 mA/cm²) | Current efficiency [cd/A] (@10 mA/cm²) | Power efficiency [lm/W] (@10 mA/cm²) |
|---|---|---|---|---|---|
| Ex. 12 | Compound 67 | 5.09 | 1091 | 10.91 | 6.74 |
| Com. Ex. 1 | Compound 74 | 5.17 | 903 | 9.03 | 5.49 |

As can be seen in Table 1, the driving voltage upon passing a current with a current density of 10 mA/cm² was 5.20 V for the compound of Example 1 of the present invention (Compound 5), 4.81 V for the compound of Example 3 of the present invention (Compound 22), and 5.09 V for the compound of Example 6 of the present invention (Compound 67), comparable to, or even lower than 5.17 V for Compound 74. The power efficiency was 6.07 lm/W for the compound of Example 1 of the present invention (Compound 5), 7.33 lm/W for the compound of Example 3 of the present invention (Compound 22), and 6.74 lm/W for the compound of Example 6 of the present invention (Compound 67), greatly higher than 5.49 lm/W for Compound 74. Further, the luminance and the current efficiency both greatly improved as compared with Compound 74.

As is clear from these results, the organic EL devices using the compounds having an acridan ring structure of the present invention can greatly improve luminous efficiency and power efficiency, and can achieve a lower actual driving voltage compared to the organic EL device that uses Compound 74.

INDUSTRIAL APPLICABILITY

The compounds having an acridan ring structure of the present invention have high hole transportability, an excellent amorphousness, and a stable thin-film state, and are desirable for organic EL devices. The organic EL device produced by using the compounds can have high luminous efficiency and high power efficiency, and a low actual driving voltage, and can thus have improved durability. There are potential applications for, for example, home electronic appliances and illuminations.

DESCRIPTION OF REFERENCE NUMERAL

1 Glass substrate
2 Transparent anode
3 Hole injection layer
4 Hole transport layer
5 Light emitting layer
6 Electron transport layer
7 Electron injection layer
8 Cathode

The invention claimed is:

1. A compound of the following general formula (1) having an acridan ring structure,

[Chemical Formula 1]

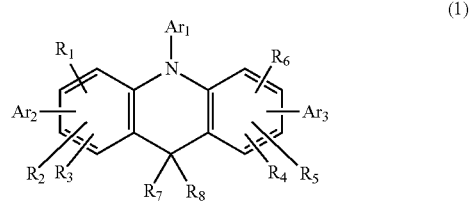

(1)

wherein $Ar_1$, $Ar_2$, and $Ar_3$ may be the same or different, $Ar_1$ represents a substituted or unsubstituted aromatic hydrocarbon group, a substituted or unsubstituted aromatic heterocyclic group, or a substituted or unsubstituted condensed polycyclic aromatic group, $Ar_2$ represents a phenyl group, a naphthyl group, a biphenyl group, or a 9,9-dimethylfluorenyl group $Ar_3$ represents a phenyl group, a naphthyl group, a biphenyl group, or a 9,9-dimethylfluorenyl group, $R_1$ to $R_6$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_7$ and $R_8$ may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, or cycloalkyloxy of 5 to 10 carbon atoms that may have a substituent, which may bind to each other via a single bond, substituted or unsubstituted methylene, an oxygen atom, or a sulfur atom to form a ring.

2. The compound having an acridan ring structure according to claim 1, wherein $R_7$ and $R_8$ in the general formula (1) are methyl.

3. The compound having an acridan ring structure according to claim 1, wherein $Ar_1$ in the general formula (1) is substituted or unsubstituted biphenylyl.

4. The compound having an acridan ring structure according to claim 1, wherein $Ar_1$ in the general formula (1) is substituted or unsubstituted 9,9-dimethylfluorenyl.

5. An organic electroluminescent device comprising a pair of electrodes, and one or more organic layers sandwiched between the pair of electrodes, wherein the compound having an acridan ring structure of claim 1 is used as a constituent material of at least one of the organic layers.

6. The organic electroluminescent device according to claim 5, wherein the organic layer is a hole transport layer.

7. The organic electroluminescent device according to claim 5, wherein the organic layer is an electron blocking layer.

8. The organic electroluminescent device according to claim 5, wherein the organic layer is a hole injection layer.

9. The organic electroluminescent device according to claim 5, wherein the organic layer is a light emitting layer.

10. A compound of the following general formula (2) having an acridan ring structure,

[Chemical Formula 2]

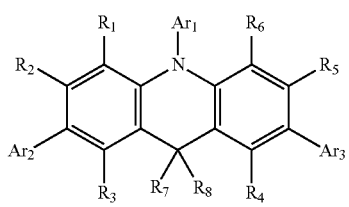

(2)

wherein $Ar_1$, $Ar_2$, and $Ar_3$ may be the same or different, $Ar_1$ represents a substituted or unsubstituted aromatic hydrocarbon group, a substituted or unsubstituted aromatic heterocyclic group, or a substituted or unsubstituted condensed polycyclic aromatic group, $Ar_2$ represents a phenyl group, a naphthyl group, a biphenyl group, or a 9,9-dimethylfluorenyl group, $Ar_3$ represents a phenyl group, a naphthyl group, a biphenyl group, or a 9,9-dimethylfluorenyl group, $R_1$ to $R_6$ may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_7$ and $R_8$ may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, or cycloalkyloxy of 5 to 10 carbon atoms that may have a substituent, which may bind to each other via a single bond, substituted or unsubstituted methylene, an oxygen atom, or a sulfur atom to form a ring.

11. An organic electroluminescent device comprising a pair of electrodes, and one or more organic layers sandwiched between the pair of electrodes, wherein the compound having an acridan ring structure of claim 10 is used as a constituent material of at least one of the organic layers.

12. The organic electroluminescent device according to claim 11, wherein the organic layer is a hole transport layer.

13. The organic electroluminescent device according to claim 11, wherein the organic layer is an electron blocking layer.

14. The organic electroluminescent device according to claim 11, wherein the organic layer is a hole injection layer.

15. The organic electroluminescent device according to claim 11, wherein the organic layer is a light emitting layer.

16. A compound of the following general formula (1) having an acridan ring structure,

[Chemical Formula 1]

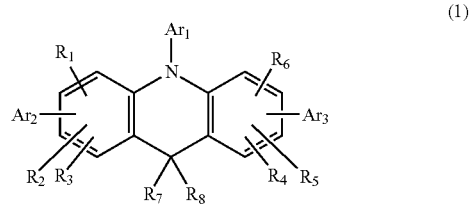

(1)

wherein $Ar_1$ $Ar_2$ and $Ar_3$ may be the same or different, $Ar_1$ represents 9-phenyl-9H-carbazolyl, $Ar_2$ represents a phenyl group, a naphthyl group, a biphenyl group, a 9,9-dimethylfluorenyl group, or a 9-phenyl-9H-carbazolyl group, $Ar_3$ represents a phenyl group, a naphthyl group, a biphenyl group, a 9,9-dimethylfluorenyl group, or a 9-phenyl-9H-carbazolyl group, $R_1$ to $R_6$ may be the same or different, and represent a hydrogen atom, a deuterium atom, a fluorine atom, a chlorine atom, cyano, trifluoromethyl, nitro, linear or branched alkyl of 1 to 6carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_7$ and $R_8$ may be the same or different, and represent trifluoromethyl, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, or cycloalkyloxy of 5 to 10 carbon atoms that may have a substituent, which may bind to each other via a single bond, substituted or unsubstituted methylene, an oxygen atom, or a sulfur atom to form a ring.

* * * * *